US005670340A

United States Patent [19]
Yabuta et al.

[11] Patent Number: 5,670,340
[45] Date of Patent: Sep. 23, 1997

[54] PROCESS FOR PRODUCING PEPTIDES IN E. COLI

[75] Inventors: Masayuki Yabuta, Tatebayashi; Yuji Suzuki, Ashikaga; Kazuhiro Ohsuye, Ohra-gun; Takehiro Oshima, Ashikaga; Seiko Onai, Isesaki; Koji Magota, Takatsuki; Shoji Tanaka, Ashiya, all of Japan

[73] Assignee: Suntory Limited, Osaka, Japan

[21] Appl. No.: 352,179

[22] Filed: Dec. 5, 1994

Related U.S. Application Data

[63] Continuation of Ser. No. 929,597, Aug. 17, 1992, abandoned.

[30] Foreign Application Priority Data

Aug. 19, 1991 [JP] Japan ................................. 3-230769
Jul. 31, 1992 [JP] Japan ................................. 4-223520

[51] Int. Cl.$^6$ .......................... C12P 21/00; C12P 21/02; C12P 21/06
[52] U.S. Cl. ...................... 435/69.4; 435/68.1; 435/69.1; 435/69.7
[58] Field of Search ................... 435/69.1, 68.1, 435/69.7, 69.4

[56] References Cited

U.S. PATENT DOCUMENTS 4,987,070  1/1991  Magota et al. ...................... 435/69.7

FOREIGN PATENT DOCUMENTS 281 418    9/1988   European Pat. Off. .
2140810   12/1984   United Kingdom .
WO 90/08194 7/1990   WIPO .

OTHER PUBLICATIONS

"Bacterial Synthesis of Recombinant α–Human Atrial Natriuretic Polypeptides", Yoshimasa Saito et al., Journal of Biochemistry, pp. 111–122, vol. 102, No. 1, Jul. 1987, Tokyo, Japan.

"Chemical Synthesis and Cloning of a Poly(arginine)–Coding Gene Fragment Designed to Aid Polypeptide Purification", C. Smith et al., Gene, pp. 321–327, vol. 32, 1984, Amsterdam NL.

Tajima, M. et al.; J. Fermantation Bioeng. 72:362–367 (Nov. 1991).

Sung. W.L. et al.; Proc. Natl. Acad. Sci. USA 83:561–565 (1986).

Guo et al. "Synthesis of human insulin gene VIII. Construction of expression vectors for fused proinsulin production in *Escherichia coli*" *Gene*, 29 pp. 251–254 (1984).

Schein. "Production of Soluble Recombinant Proteins in Bacteria", *Biotechnology*, vol. 7, pp. 1141–1147 (1989).

Skoog et al. "Calculation of the isoelectric points of polypeptides from the amino acid composition", *Trends Anal. Chem.*, vol. 5, No. 4, pp. 82–83 (1986).

Itakura et al. "Expression in *Escherichia coli* of a Chemically Synthesized Gene for the Hormone Somatostatin", *Science*, vol. 198, pp. 1056–1063 (1977).

Goeddel et al. "Expression of *Escherichia coli* of chemically synthesized genes for human insulin", *Proc. Natl. Acad. Sci.*, USA, vol. 76, No. 1, pp. 106–110 (1979).

Shine et al. "Expression of cloned β–endorphin gene sequences by *Escherichia coli*, *Nature*," vol. 285, pp. 456–461 (1980).

*Primary Examiner*—Eric Grimes
*Attorney, Agent, or Firm*—Burns, Doane, Swecker & Mathis, L.L.P.

[57] ABSTRACT

The present invention is a process to express a target peptide in a large amount and accumulate the target peptide in host cells in the form of inclusion bodies. The process comprises:

A) culturing host cells transformed with a plasmid able to express a gene coding for a fusion protein represented in the formula A—L—B, wherein B is a target peptide, A is a protective peptide comprising a 90-210 amino acid fragment *E. coli* β-galactosidase, and L is a linker peptide positioned between the C-terminus of the protective peptide and the N-terminus of the target peptide and selected so that when the fusion protein is treated by an enzyme or chemical substance, the target peptide is separated, and wherein the protective peptide and linker peptide are selected so that the isoelectric point of the fusion protein in between 4.9 and 6.9;

B) obtaining an insoluble fraction comprising inclusion bodies by homogenization of th cultured transformed cells;

C) solubilizing the fusion protein in the inclusion bodies by treatment of the insoluble fraction with a solubilizing agent; and, D) cleaving the peptide bond between the C-terminus of the linker peptide and the N-terminus of the target peptide of the solubilized fusion protein to release the target peptide from the other peptides followed by purification of the target peptide.

5 Claims, 16 Drawing Sheets

Fig. 5

R1: 5'-AATTCTCGGGCTCGCCACTTCGGGCTCATC-3' (SEQ ID NO:2)
    3'-GAGCCCGAGCGGTGAAGCCCGAGTAGAGCT-5' (SEQ ID NO:3)

R3: 5'-AATTCCGGCCTATATCGCCGAC-3' (SEQ ID NO:4)
    3'-GGCGGATATAGCGGGCTGAGCT-5' (SEQ ID NO:5)

R4: 5'-AATTCCGGGCATCACCGGGCCGCCACAGGC-3' (SEQ ID NO:6)
    3'-GGCCGTAGTGGCCCGGTGTCCGAGCT-5' (SEQ ID NO:7)

R5: 5'-AATTCCGGCCTATATCGCCGACATCACCGATGGGGAAGAC-3' (SEQ ID NO:8)
    3'-GGCGGATATAGCGGCTGTAGTGGCTACCCCTTCTGAGCT-5' (SEQ ID NO:9)

Fig. 6 pG97S4DhCT[G] : β-gal97S4D-EF-LE-hCT[G]
                                EcoRI Xhol

| Construct | Sequence |
|---|---|
| pG97S4D hCT[G]R10 | EF—RHHRRHRCGCWRLYRRHHRWGRSGSPLRAHEQF—LE |
| pG97S4D hCT[G]R8 | EF—RHHRRLYRRHHRWGRSGSPLRAHEQF—LE |
| pG97S4D hCT[G]R6 | EL—RLYRRHHRWGRSGSPLRAHEQF—LE |
| pG97S4D hCT[G]R5 | EF—RLYRRHHRWGR—LE |
| pG97S4D hCT[G]R4 | EF—RHHRRHR—LE |
| pG97S4D hCT[G]R3 | EF—RLYRR—LE |
| pG97S4D hCT[G]R1 | EF—SGSPLRAH—LE |

R : ARGININE RESIDUE

1. MOLECULAR WEIGHT MARKER
2. W3110/ pG97S4DhCT[G]
3. W3110/ pG97S4DhCT[G]R1
4. W3110/ pG97S4DhCT[G]R3
5. W3110/ pG97S4DhCT[G]R4
6. W3110/ pG97S4DhCT[G]R5
7. W3110/ pG97S4DhCT[G]R6
8. W3110/ pG97S4DhCT[G]R8
9. W3110/ pG97S4DhCT[G]R10
10. MOLECULAR WEIGHT MARKER

Fig. 9a

AMINO ACID SEQUENCE AND DNA SEQUENCE

GlyLeuSerLysGlyCysPheGlyLeuLysLeuAspArgIleGlySerMetSerGlyLeuGlyCys *

GGCTTGTCCAAGGGCTGCTTCGGCCTCAAGCTGGACCGAATCGGCTCCATGAGCGGCCTGGGATGTTAG (SEQ ID NO:10)
CCGAACAGGTTCCCGACGAAGCCGGAGTTCGACCTGGCTTAGCCGAGGTACTCGCCGGACCCTACAATC

Fig. 9b

DESIGN OF PRIMERS

PRIMER 1

EcoRI  XhoI

5'—TAA<u>GAATTC</u>|CTCGAG|GGCTTGTCCAAGGGCT—3'  (SEQ ID NO:11)

PRIMER 2

3'—TCGCCGCCCGGGACCCTACAATT|CAGCTG|AAT—5'  (SEQ ID NO:12)

Sal I

<u>_____</u> UNDERLINE SHOWS DNA REQUENCE WHERE PRIMER MATCHES CNP GENE

☐ RESTRICTION ENZYME SITE NEWLY INTRODUCED INTO GENE

GluPheArgArgArgGluPheLeuGlu
AATTCCGGGCGCCGAGAGTTCC          (SEQ ID NO:13)
    GGCCGCGGGCTCTCAAGGAGCT      (SEQ ID NO:14)

R5-2

GluPheArgArgHisHisArgArgGluPheLeuGlu
AATTCCGGGCGCCATCACCGGGCGCCACCGAGAGTTCC          (SEQ ID NO:15)
    GGCCGCGGTAGTGGCCCGCGGTGGCTCTCAAGGAGCT       (SEQ ID NO:16)

R5-3

GluPheArgArgArgArgGluPhe
AATTTCGACGCCCGTCGCCGAG              (SEQ ID NO:17)
    AGCTGCGGGCAGCGGCTCTTAA          (SEQ ID NO:18)

1. MOLECULAR WEIGHT MARKER
2. W3110/ pG97S4DhCNP-22
3. W3110/ pG97S4DhCNP-22 R3-2
4. W3110/ pG97S4DhCNP-22 R5-2
5. W3110/ pG97S4DhCNP-22 R5-3

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 99 base pairs
        ( B ) TYPE: nucleic acid
        ( C ) STRANDEDNESS: double
        ( D ) TOPOLOGY: linear ( v i i ) IMMEDIATE SOURCE:
        ( B ) CLONE: plasmid pBR322

( i x ) FEATURE:
        ( A ) NAME/KEY: CDS
        ( B ) LOCATION: 1..99

( x i ) SEQUENCE DESCRIPTION: SEQ ID NO:1:

```
CGG  CAT  CAC  CGG  CGC  CAC  AGG  TGC  GGT  TGC  TGG  CGC  CTA  TAT  CGC  CGA     48
Arg  His  His  Arg  Arg  His  Arg  Cys  Gly  Cys  Trp  Arg  Leu  Tyr  Arg  Arg
 1                  5                        10                       15

CAT  CAC  CGA  TGG  GGA  AGA  TCG  GGC  TCG  CCA  CTT  CGG  GCT  CAT  GAG  CAA     96
His  His  Arg  Trp  Gly  Arg  Ser  Gly  Ser  Pro  Leu  Arg  Ala  His  Glu  Gln
               20                        25                       30

TTC                                                                                 99
Phe
```

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AATTCTCGGG CTCGCCACTT CGGGCTCATC         30

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TCGAGATGAG CCCGAAGTGG CGAGCCCGAG        30

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AATTCCGCCT ATATCGCCGA C        21

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

TCGAGTCGGC GATATAGGCG G        21

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AATTCCGGCA TCACCGGCGC CACAGGC        27

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

TCGAGCCTGT GGCGCCGGTG ATGCCGG        27

( 2 ) INFORMATION FOR SEQ ID NO:8:

( i ) SEQUENCE CHARACTERISTICS:
        ( A ) LENGTH: 39 base pairs
        ( B ) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO:8:

AATTCCGCCT ATATCGCCGA CATCACCGAT GGGGAAGAC                                39

(2) INFORMATION FOR SEQ ID NO:9:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

TCGAGTCTTC CCCATCGGTG ATGTCGGCGA TATAGGCGG                                 39

(2) INFORMATION FOR SEQ ID NO:10:

(i) SEQUENCE CHARACTERISTICS:
            (A) LENGTH: 69 base pairs
            (B) TYPE: nucleic acid
            (C) STRANDEDNESS: double
            (D) TOPOLOGY: linear (vii) IMMEDIATE SOURCE:
            (B) CLONE: plasmid pUCCNP1

(ix) FEATURE:
            (A) NAME/KEY: CDS
            (B) LOCATION: 1..69

(xi) SEQUENCE DESCRIPTION: SEQ ID NO:10:

GGC TTG TCC AAG GGC TGC TTC GGC CTC AAG CTG GAC CGA ATC GGC TCC           48
Gly Leu Ser Lys Gly Cys Phe Gly Leu Lys Leu Asp Arg Ile Gly Ser
 1               5                  10                  15

ATG AGC GGC CTG GGA TGT TAG                                               69
Met Ser Gly Leu Gly Cys
        20

(2) INFORMATION FOR SEQ ID NO:11:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

TAAGAATTCC TCGAGGGCTT GTCCAAGGGC T                                         31

(2) INFORMATION FOR SEQ ID NO:12:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

TAAGTCGACT AACATCCCA GGCCGCCGCT                                            30

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
AATTCCGGCG CCGAGAGTTC C                                          21
```

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
TCGAGGAACT CTCGGCGCCG G                                          21
```

( 2 ) INFORMATION FOR SEQ ID NO:15:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
AATTCCGGCG CCATCACCGG CGCCACCGAG AGTTCC                          36
```

( 2 ) INFORMATION FOR SEQ ID NO:16:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
TCGAGGAACT CTCGGTGGCG CCGGTGATGG CGCCGG                          36
```

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

```
AATTTCGACG CCGTCGCCGA G                                          21
```

( 2 ) INFORMATION FOR SEQ ID NO:18:

( i ) SEQUENCE CHARACTERISTICS:
        ( A ) LENGTH: 21 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

AATTCTCGGC GACGGCGTCG A                    21

(2) INFORMATION FOR SEQ ID NO:19:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Glu Phe Arg His His Arg Arg His Arg Cys Gly Cys Trp Arg Leu Tyr
 1               5                  10                  15

Arg Arg His His Arg Trp Gly Arg Ser Gly Ser Pro Leu Arg Ala His
                20                  25                  30

Glu Gln Phe Leu Glu
            35

(2) INFORMATION FOR SEQ ID NO:20:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Glu Phe Arg His His Arg Arg Leu Tyr Arg Arg His His Arg Trp Gly
 1               5                  10                  15

Arg Ser Gly Ser Pro Leu Arg Ala His Glu Gln Phe Leu Glu
                20                  25                  30

(2) INFORMATION FOR SEQ ID NO:21:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Glu Leu Arg Leu Tyr Arg Arg His His Arg Trp Gly Arg Ser Gly Ser
 1               5                  10                  15

Pro Leu Arg Ala His Glu Gln Phe Leu Glu
                20                  25

(2) INFORMATION FOR SEQ ID NO:22:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide ( x i ) SEQUENCE DESCRIPTION: SEQ ID NO:22:

Glu Phe Arg Leu Tyr Arg Arg His His Arg Trp Gly Arg Leu Glu
1               5                   10                  15

( 2 ) INFORMATION FOR SEQ ID NO:23:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

Glu Phe Arg His His Arg Arg His Arg Leu Glu
1               5                   10

( 2 ) INFORMATION FOR SEQ ID NO:24:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

Glu Phe Arg Leu Tyr Arg Arg Leu Glu
1               5

( 2 ) INFORMATION FOR SEQ ID NO:25:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

Glu Phe Ser Gly Ser Pro Leu Arg Ala His Leu Glu
1               5                   10

( 2 ) INFORMATION FOR SEQ ID NO:26:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

Glu Phe Arg Arg Arg Glu Phe Leu Glu
1               5

( 2 ) INFORMATION FOR SEQ ID NO:27:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

```
Glu Phe Arg Arg His His Arg Arg His Arg Glu Phe Leu Glu
1               5                   10
```

( 2 ) INFORMATION FOR SEQ ID NO:28:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:28:

```
Glu Phe Arg Arg Arg Arg Arg Glu Phe
1               5
```

PROCESS FOR PRODUCING PEPTIDES IN E. COLI

This application is a continuation of application Ser. No. 07/929,597, filed Aug. 17, 1992, now abandoned.

BACKGROUND OF THE INVENTION

1. Field of the Invention

The present invention relates to a method for producing a physiologically active peptides or their precursor (may be referred to as the target peptide in the present invention) as a fusion protein which has an isoelectric point towards the acidic pH.

2. Related Arts

There have thus far been numerous efforts made to produce physiologically active peptides or proteins in microorganisms such as *Escherichia coli* using recombinant DNA technology. In such cases, when short peptides having relatively low molecular weights were produced by direct expression systems using microorganisms such as *Escherichia coli*, the short peptide ends up being rapidly broken down within the microorganism.

In order to inhibit this degradation, a method is used in which after typically producing the target peptide in the form of a fusion protein with other proteins or polypeptides (to be referred to as the protective peptide), chemical or enzymatic treatment is performed to specifically release the target peptide from the fusion protein followed by separation and purification.

A known method for releasing the target peptide from the fusion protein, in the case the molecules of said target peptide do not contain a methionine residue, comprises of producing a fusion protein in which a methionine residue is introduced at the C-terminal amino acid position of a linker peptide between a protective peptide and the target peptide, followed by cleavage of the methionine residue by treatment with cyanogen bromide (CNBr) to release the target peptide (Science, 198, 1059 (1977), Proc. Natl. Acad. Sci., 76, 106 (1978).

In addition, in the case the molecule of the target peptide does not contain an arginine residue or lysine residue, after producing a fusion protein in which an arginine residue or lysine residue is introduced at C-terminal amino acid position of a linker peptide between a protective peptide and the target peptide, methods can be used to release the target peptide comprising treatment with trypsin which specifically cleaves the C-terminal of the arginine residue or lysine residue (Nature, 285, 456 (1980), and treatment with lysyl endopeptidase (Achromobacter protease I) which specifically releases the C-terminal of the lysine residue.

Fragment of protein originating in the host microorganism used in production is commonly used for the protective peptide to of produce the fusion protein. In such cases, a polypeptide of a suitable size (length) from the N-terminal (amino terminal region) of a protein, expressed in large amounts in the cells of the host microorganism, is used, and it is known that the length of that polypeptide has a considerable influence on the productivity of the fusion protein.

For example, although it can be considered to improve productivity by reducing the size (shortening the length) of said protective peptide region to increase the relative proportion of target protein with respect to said fusion protein, reduction of said protective peptide region does not always improve productivity of the target peptide. For example, when insulin was produced in *Escherichia coli* as a fusion protein, although the productivity of insulin temporarily increased when β-galactosidase was used for the protective peptide and the size of the β-galactosidase was reduced, it is known that insulin productivity decreased by further reduction of the size (Gene, 29, 251, 1984).

As such, in the case of producing a target peptide as a portion of a fusion protein, there is no established theory as to how large the protective peptide should be despite the size of the protective peptide being closely related to the stability of the fusion protein inside the microorganism. In general, stable fusion proteins form insoluble inclusion bodies in host cells. In other words, in order to produce a large amount of fusion protein it is advantageous to form inclusion bodies in host cells.

However, depending on the particular case, when the number of inclusion bodies expressed per cell is increased, the inclusion bodies cause damage to the cells resulting in inhibition of cell growth which may decrease the productivity of inclusion bodies per volume of culture. Although the mechanism of formation of inclusion bodies in microorganism is described in detail in the paper by Schein (Biotechnology, 7, 1141 (1989)), numerous factors are involved in inclusion body formation, and there is no established theory at present. In addition, there are also no established methods for large-scale production on an industrial scale by expressing fusion protein as stable inclusion bodies in microorganism.

There are numerous reports of methods in which human calcitonin is produced as a fusion protein in *Escherichia coli*. For example, Bennett et al. reported a method for producing human calcitonin precursor (hCT-Gly) by expressing a fusion protein of the chloramphenicol acetyltransferase and human calcitonin precursor (hCT-Gly) (Unexamined Patent Publication No. 60-501391). However, this method has a low level of efficiency with only 1.1–2.0 mg of human calcitonin precursor obtained from 44 mg of fusion protein.

On the other hand, the inventors of the present invention reported a method for extremely efficiently producing a fusion protein of the *Escherichia coli* β-galactosidase and human calcitonin precursor (hCT-Gly-Lys-Lys-Arg) as an inclusion bodies in *Escherichia coli* (Unexamined Patent Publication No. 64-10999). Moreover, a method for producing human calcitonin was disclosed by the inventors of the present invention wherein after solubilizing the fusion protein (as described above with urea, human calcitonin precursor (hCT-Gly-Lys-Lys-Arg) was released from the fusion protein with V8 protease, hCT-Gly was obtained by removing Lys-Lys-Arg of the C-terminal portion of human calcitonin precursor using carboxypeptidase B, and the mature C-terminal amidated human calcitonin was obtained with high efficiency using a *Xenopus laevis* C-terminal amidation enzyme (Unexamined Patent Publication No. 2-190193).

However, there is still a need for an efficient method for producing peptide.

SUMMARY OF THE INVENTION

Thus, the present invention provides a method for efficiently producing a large amount of physiologically active peptide or its precursor.

As a result of the inventors of the present invention studying a means of solving the above-mentioned objects, it was experimentally verified for the first time that in order to improve the productivity of fusion protein in *Escherichia coli* cells, the isoelectric point of a fusion protein possessing within the range of pI 4.9 to pI 6.9 leads to high level of stability and productivity of said fusion protein. In addition, completely new findings were obtained wherein the above-mentioned objects are solved by regulating the number of amino acids having a charge within the linker peptide (basic or acidic amino acid residues) to adjust the isoelectric point of the fusion protein to within a range of pI 4.9 to pI 6.9.

Thus, the present invention provides a process for producing physiologically active peptide or its precursor (target peptide) comprising:
A) culturing host cells transformed with expression plasmid able to express a gene coding for a fusion protein represented in the following formula:

A—L—B wherein, B is a target peptide, A is a protective peptide comprised of 90–200 amino acid residues, and L is a linker peptide positioned between the C-terminal of said protective peptide and the N-terminal of said target peptide and selected so that said fusion protein is treated by an enzyme or chemical substance, the above-mentioned target peptide is separated, and said protective peptide and linker peptide are selected so that the isoelectric point of the entire fusion protein A—L—B is within a range of 4.9–6.9; 0

B) obtaining an insoluble fraction comprising inclusion bodies by homogenization of the cultured cells of said transformant;

C) solubilizing a fusion protein in said inclusion bodies by treatment of said insoluble fraction with solubilizing agent; and, D) cleaving the peptide bond between the C-terminal of the linker amino acid residue and the N-terminal of the target peptide of said solubilized fusion protein to release said target peptide from the other peptide.

BRIEF DESCRIPTION OF THE DRAWINGS

FIG. 5 indicates the nucleotide sequences of R1 through R5 which are DNA coding for the linker portions. These sequences are also indicated in SEQ ID NOS 2 to 9.

FIG. 6 indicates the amino acid sequence of each linker peptide. [SEQ ID NOS: 19–25]

FIGS. 9A and 9B indicate the amino acid sequence of CNP-22 [SEQ ID. NO: 10], the nucleotide sequence coding for it, and the PCR primers for insertion of restriction enzyme sites to both ends [SEQ ID. NOS: 11 and 12].

FIG. 11 indicates a linker peptide for adjusting the isoelectric point of a fusion protein and an oligonucleotide sequence coding for it [SEQ ID. NOS 13–18] and [SEQ ID NO 26].

Figure 1:
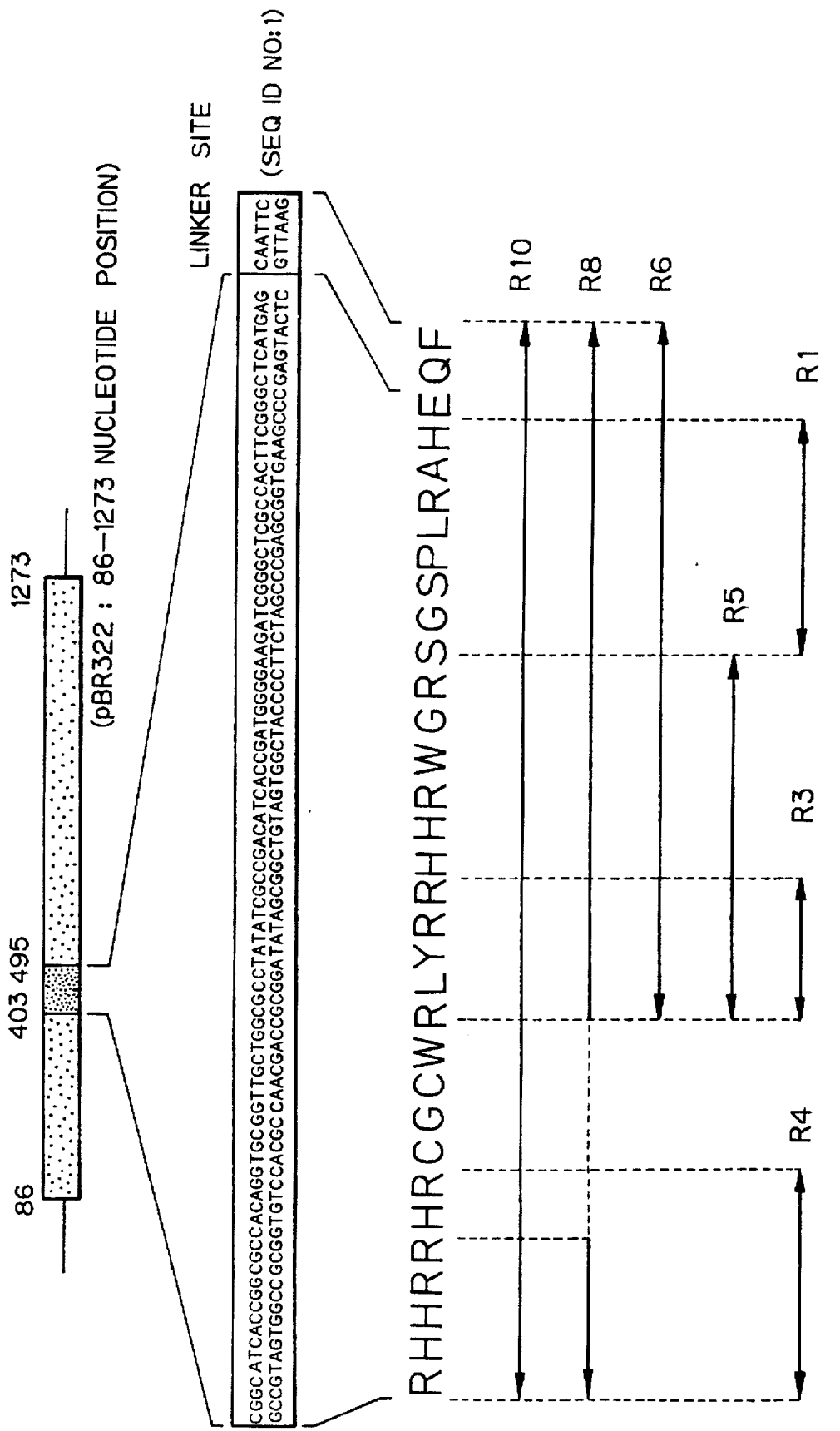
FIG. 1 indicates the nucleotide sequence of a portion of the tetracycline resistant gene of nucleotide positions 403–495 within plasmid pBR322, the corresponding amino acid sequence and the portions coding for each linker peptide. This nucleotide sequence is indicated in SEQ ID NO 1.

The method of the present invention can be applied for production of a fusion protein of physiologically active peptides (target peptides), and particularly, to its production via its inclusion bodies. In addition to human calcitonin explained in detail in the present invention, examples of such peptides include non-human calcitonins and precursors, thereof natriuretic peptides (NP) such as ANP, BNP and CNP, cell growth factors and parathyroid hormone (PTH). However, the peptides to which the present process is applied are not limited to these peptides.

The protective peptide in the present invention is preferably a peptide inherently possessed by the host. For example, in the case of using *Escherichia coli* for the host, it is preferable to use β-galactosidase of *Escherichia coli* or a portion thereof. In the case of using a portion of β-galactosidase of *Escherichia coli*, it is preferable to use its N-terminal portion. For example, use of the portion consisting of 90–210 amino acids of the N-terminal side is preferable. Particularly preferable protective peptides are peptides consisting of the 1st to 97th amino acids of the N-terminal of *Escherichia coli* β-galactosidase. It is even more preferable to use peptides wherein the cysteine residue is substituted by a serine residue in a peptide consisting of these 97 amino acid residues. Furthermore, it is most preferable to use a peptide wherein the cysteine residue is substituted by a serine residue in a peptide consisting of the above-mentioned 97 amino acid residues, and moreover, four glutamic acid residues are substituted by aspartic acid residues.

The present invention is characterized by the production of the target peptide in the form of a fusion protein having an isoelectric point between 4.9 and 6.9. In this case, the isoelectric point of the fusion protein can be determined in the following manner from the amino acid sequence. Furthermore, the method for calculating the isoelectric point should be in accordance with the method described in Trends in Analytical Chemistry, Vol. 5, No. 4, pp. 82–83 (1986). For example, an isoelectric point estimation program of DNASIS (Hitachi) prepared based on this method can be used.

In order to regulate the isoelectric point of the fusion protein within the above-mentioned range, the amino acid residues of the protective peptide and/or linker peptide are regulated since the amino acids of the target peptide cannot be altered. In this case, natural peptide or portion of those peptide that gives the above-mentioned isoelectric point can be selected for the protective peptide and/or linker peptide that form a fusion peptide with the target peptide. Another method involves regulation of the isoelectric point of the fusion protein by substitution, elimination or addition of amino acid residues of natural peptides or portions of those peptides.

The addition or elimination of acidic amino acid such as aspartic acid or glutamic acid residue, the addition or elimination of basic amino acid such as arginine or lysine residue, substitution of other amino acid by such an amino acid, or combination of these amino acid manipulations can be used for this regulation.

As mentioned above, regulation of the isoelectric point of the fusion protein can be performed with either the protective peptide or linker peptide or both.

A peptide or a portion thereof that can be coded by the 403rd to 495th nucleotide sequence of the tetracycline-resistant gene derived from pBR322 can be used for this type of peptide. As is indicated in FIG. 1 and SEQ ID NO 1, this gene region can code for 10 arginine residues among 33 amino acid residues, and by using the various portions in this region, various linker peptides can be obtained containing different numbers of arginine residues. In this case, it is preferable to use a portion containing 1 or more, preferably 3 or more and particularly preferably 3 to 8 amino acids.

In order to release a target peptide from a fusion protein, it is necessary that an amino acid residue that can be enzymatically or chemically cleaved be present at the C-terminal of a linker peptide. Examples of these amino acid residues that are used include an arginine residue or lysine residue cleaved by trypsin, a lysine residue cleaved by lysyl endopeptidase, a glutamine residue cleaved by V8 protease, and a methionine residue cleaved with cyanogen bromide.

Next, the following provides an explanation of production of a plasmid that expresses a fusion protein taking the example in which the target peptide is human calcitonin precursor.

Plasmid pG97S4DhCT(G) is used as a starting plasmid for constructing expression plasmids for a expressing human calcitonin precursor comprising the amino acid sequence of human calcitonin and a glycine residue added to its C-terminal in form of fusion proteins containing various linkers.

Figure 2:
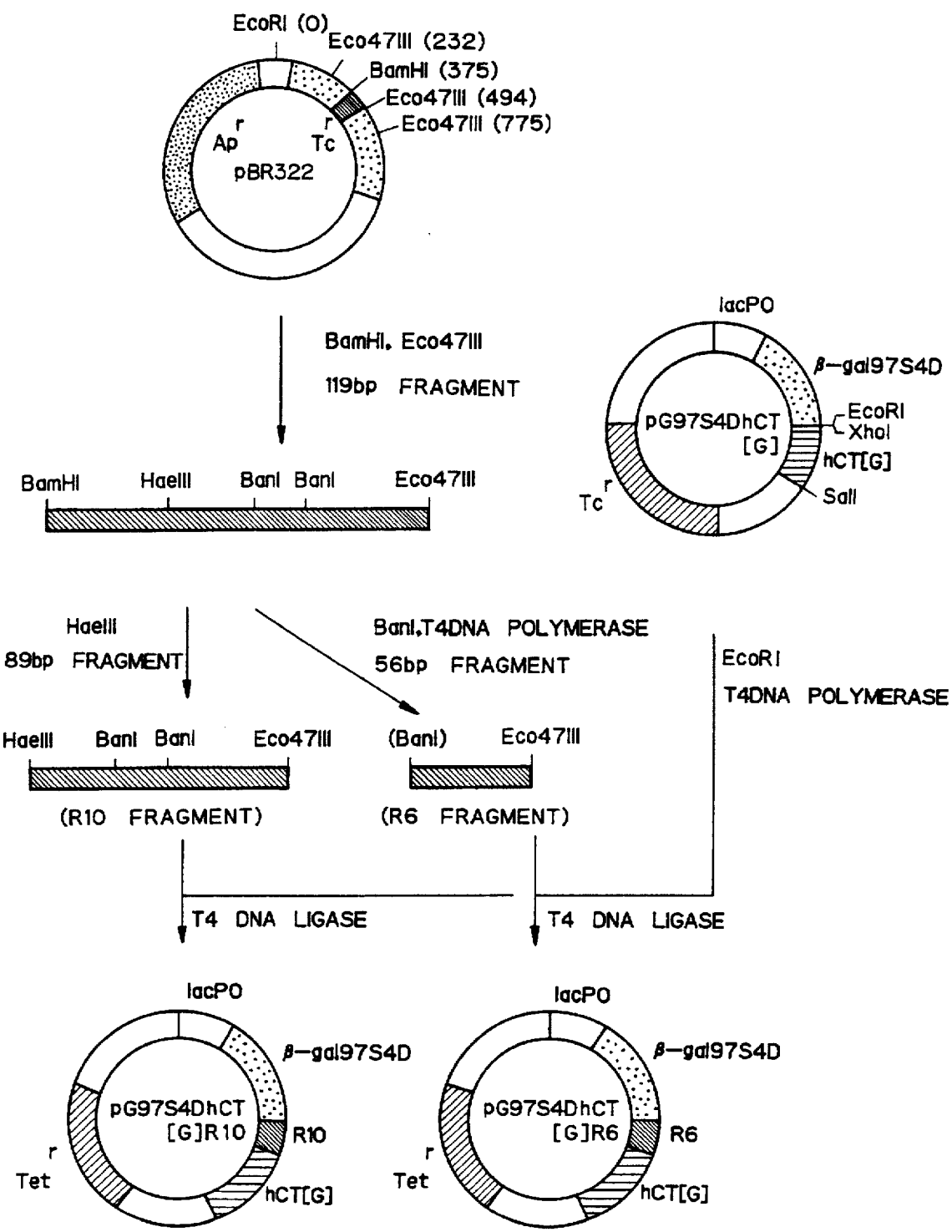
FIG. 2 indicates a process for construction of plasmids pG97S4DhCT(G)R10 and pG97S4DhCT(G)R6.

In this plasmid, the structural gene (β-gal97S4D) coding for a protective peptide consisting of 97 amino acids of the N-terminal of *Escherichia coli* β-galactosidase, wherein a cysteine residue contained therein is substituted by a serine residue, and four glutamic acid residues are substituted by aspartic acid residues, and a structural gene of human calcitonin precursor are linked via the EcoRI and XhoI recognition sites as indicated in FIG. 2. The structural gene coding for this fusion protein is under the control of the lac promoter. Moreover, this plasmid contains a gene for a selection marker.

This plasmid is derived from pG97SHPCTLE(G) plasmid described in Unexamined Patent Publication No. 2-190193. *Escherichia coli* W3110 containing the above-mentioned pG97S4DhCT(G) plasmid was deposited to the Fermentation Research Institute, Agency of Industrial Science and Technology, as *Escherichia coli* SBM323 on Aug. 8, 1991 based on the provisions of the Budapest treaty, and given FERM BP-3503.

A fusion protein encoded by pG97S4DhCT(G) plasmid comprises a protective peptide consisting of 97 amino acids of the end of the N-terminal of β-galactosidase, in which the cysteine residue contained therein is substituted by a serine residue, and 4 glutamic acid residues are substituted by aspartic acid residues, and the above-mentioned human calcitonin precursor. Its expression is extremely low, and its isoelectric point is 4.43. Thus, in order to express various fusion proteins over a broad range of isoelectric basic amino acid, DNA sequences coding for linker peptides having various basic amino acid residues are inserted between the above-mentioned β-galactosidase gene and human calcitonin precursor gene using the EcoRI-XhoI site.

It is convenient to use a peptide comprising 33 amino acids able to be encoded by a gene derived from the tetracycline-resistant gene of nucleotide position 86-1273 of plasmid pBR322, or a portion of said peptide, for a linker peptide. Ten arginine residues are distributed in this peptide region, and by using suitable portions for the linker peptide, fusion proteins can be obtained having various isoelectric points.

The linker peptides obtained from this region along with the nucleotide sequences that code for such linker peptides are indicated in FIG. 1. The genes that code for these peptides are obtained by digestion of plasmid pBR322 with a suitable restriction enzyme, or by chemical synthesis in accordance with a commonly used method. These linker peptides $R_1$, $R_3$, $R_4$, $R_5$, $R_6$, $R_8$ and $R_{10}$ contain 1, 3, 4, 5, 6, 8 and 10 arginine residues, respectively. The expression plasmids in which a gene cloning for one of these linker peptides is inserted at the EcoRI-XhoI site in the above-mentioned plasmid pG97S4DhCT(G) are referred to as pG97S4DhCT(G)R1, pG97S4DhCT(G)R3, pG97S4DhCT(G)R4, pG97S4DhCT(G)R5, pG97S4DhCT(G)R6, pG97S4DhCT(G)R8 and pG97S4DhCT(G)R10.

In addition, *Escherichia coli* W3110 strains obtained by transformation with the above-mentioned starting plasmid and these plasmids are referred to as W3110/pG97S4DhCT(G), W3110/pG97S4DhCT(G)R1, W3110/pG97S4DhCT(G)R3, W3110/pG97S4DhCT(G)R4, W3110/pG97S4DhCT(G)R5, W3110/pG97S4DhCT(G)R6, W3110/pG97S4DhCT(G)R8 and W3110/pG97S4DhCT(G)R10.

The following results are obtained when the isoelectric points of the fusion proteins produced by these microorganisms are calculated:

W3110/pG97S4DhCT(G) (the number of arginine residues in linker region=0); isoelectric point=4.43, W3110/pG97S4DhCT(G)R1 (the number of arginine residues in linker region=1); isoelectric point=4.70, W3110/pG97S4DhCT(G)R3 (the number of arginine residues in linker region=3); isoelectric point=4.90, W3110/pG97S4DhCT(G)R4 (the number of arginine residues in linker region=4); isoelectric point=5.80, W3110/pG97S4DhCT(G)R5 (the number of arginine residues in linker region=5); isoelectric point=5.91, W3110/pG97S4DhCT(G)R6 (the number of arginine residues in linker region=6); isoelectric point=6.01, W3110/pG97S4DhCT(G)R8 (the number of arginine residues in linker region=8); isoelectric point=6.83, and W3110/pG97S4DhCT(G)R10 (the number of arginine residues in linker region=10); isoelectric point=7.85.

*Escherichia coli* transformants producing the above-mentioned fusion protein having an isoelectric point from 4.43 to 7.85 were cultured, and analyzed for the amount of fusion protein produced per number of cells by SDS polyacrylamide gel electrophoresis. Strain W3110/pG97S4DhCT(G) having an isoelectric point of 4.43 and strain W3110/pG97S4DhCT(G)R1 having an isoelectric point of 4.70 produced only a small amount of fusion protein. It was also verified that the other strains produced a large amount of fusion protein as inclusion bodies in bacterial cells. Thus, it was indicated by these results that if the isoelectric point of the fusion protein is in the vicinity of 4.5–4.7, both the productivity of fusion protein and the amount of inclusion bodies produced are poor.

Moreover, although the productivity of fusion protein per number of cells in the case of strain W3110/pG97S4DhCT (G)R10 having an isoelectric point of 7.85 was roughly equivalent to that of the other bacterial strains, it was verified that the final bacterial concentration during culturing was only half that of other strains. It is believed that although the capacity to form fusion protein per number of cells increased, due to the isoelectric point of the fusion protein being weakly alkaline of pI 7.85 inhibition of cell growth occurred due to rapid formation of inclusion bodies or the isoelectric point of the fusion protein being weakly alkaline, thus resulting in an absence of increase in final bacterial concentration.

Based on the above results, it was verified for the first time by the inventors of the present invention that in order to produce fusion protein both stably and in a large amount within *Escherichia coli* cells in the form of inclusion bodies, it is important that the isoelectric point of the fusion protein be within the acidic pI between 4.9 and 6.9.

Next, the inventors of the present invention efficiently performed separation and purification of human calcitonin precursor (hCT-Gly) from inclusion bodies of fusion protein of human calcitonin precursor produced in *Escherichia coli* in the manner described above. Moreover, it was verified that human calcitonin having the amidated C-terminal can be efficiently produced using amidation enzyme derived from *Xenopus laevis*.

The following provides another example of the present invention for construction of a plasmid that expresses a fusion protein taking as an example the case wherein the target peptide is human C-type natriuretic peptide-22 (to be abbreviated as CNP-22) (SEQ ID NO. 10). Plasmid pG97S4DhCNP-22 was used as a starting plasmid for construction of expression plasmids for expressing human CNP-22 comprising 22 amino acids as fusion proteins containing various linkers.

Figure 10:
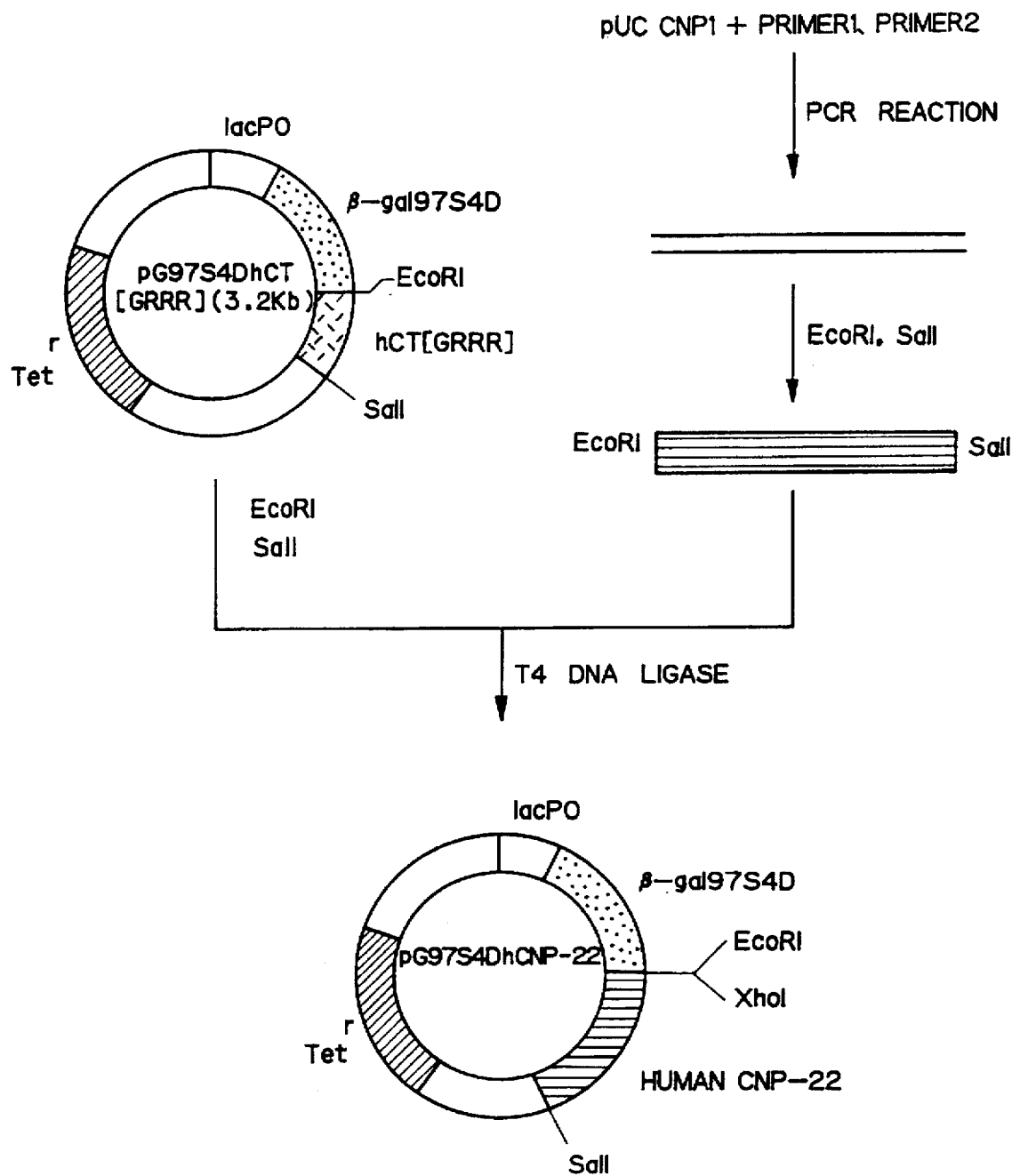
FIG. 10 indicates a process for construction of plasmid pG97S4DhCNP-22.

In this plasmid, the structural gene (βgal97S4D) coding for a protective peptide consisting of 97 amino acids of the N-terminal of *Escherichia coli* β-galactosidase wherein a cysteine residue contained therein is substituted by a serine residue and four glutamic acid residues are substituted by aspartic acid residues, and the structural gene of human CNP-22, are linked via the EcoRI and XhoI recognition sites as indicated in FIG. 10. The structural gene coding for this fusion protein is under the control of the lac promoter. Moreover, this plasmid contains a resistance marker for tetracycline resistance.

In the construction of the pG97S4DhCNP-22 expression plasmid, a human CNP-22 structural gene and the plasmid pUCCNP1 used for preparation of said gene are disclosed in Unexamined Patent Publication No. 4-139199. In addition, plasmid pG97S4DhCT(GRRR) used as a plasmid which codes for a protective peptide is essentially identical to the above-mentioned plasmid pG97S4DhCT(G).

The isoelectric point of the fusion protein encoded by plasmid pG97S4DhCNP-22 is 4.56. From the viewpoint that the isoelectric point of the fusion protein for high expression of fusion protein indicated above is preferably within the range of pI=4.9 to pI=6.9, production of a large amount of fusion protein cannot be expected. As such, a study was conducted wherein linker peptide genes coding for various basic amino acids were inserted into the EcoRI-XhoI region between the above-mentioned β-galactosidase gene and human CNP gene for the purpose of designing various fusion proteins having isoelectric points from 4.9 to 6.9 and expressing a large amount of said fusion proteins in *Escherichia coli*.

These linker peptides can be produced using method wherein genes coding for basic amino acids are artificially designed followed by chemical synthesis.

FIG. 11 indicates the design of linker peptide genes coding for basic amino acids and the chemically synthesized gene sequences. These linker peptides, R3-2 (SEQ ID NOs 13 and 14), R5-2 (SEQ ID NOs 15 and 16), and R5-3 (SEQ ID NOs 17 and 18) contain 3, 5 and 5 arginine residues, respectively. The expression plasmids wherein genes coding for these linker peptides have been inserted into the EcoRI-XhoI region in the above-mentioned pG97S4DhCNP-22 are referred to as pG97S4DhCNP-22R3-2, pG97S4DhCNP-22R5-2 and pG97S4DhCNP-22R5-3, respectively.

In addition, *Echerichia coli* W3110 strains obtained by transformation with the above-mentioned starting plasmids and these plasmids are referred to as W3110/pG97S4DhCN-22, W3110/pG97S4DhCNP-22R3-2, W3110/pG97S4DhCNP-22R5-2, and W3110/pG97S4DhCNP-22R5-3, respectively.

The following results are obtained when the isoelectric points of the fusion proteins produced by these microorganisms are calculated:

W3110/pG97S4DhCNP-22 (the number of arginine residues in linker region=0); isoelectric point=4.56.

W3110/pG97S4DhCNP-22R3-2 (the number of arginine residues in linker region=3); isoelectric point=4.95, W3110/pG97S4DhCNP-22R5-2 (the number of arginine residues in linker region=5); isoelectric point=6.22, and W3110/pG97S4DhCNP-22R5-3 (the number of arginine residues in linker region=5); isoelectric point=5.59.

When the *Escherichia coli* strains producing the above-mentioned fusion protein having isoelectric points from pI 4.56 to pI 6.22 were cultured, and analyzed for the amount of fusion protein produced per number of cells by SDS polyacrylamide gel electrophoresis, although the amount of fusion protein produced by strain W3110/pG97S4DhCNP-22 (isoelectric point of fusion protein=4.56) was not that high, in the case of those strains that demonstrated fusion protein isoelectric points from pI 4.95 to pI 6.22, it was verified that the amount of fusion protein expressed was large in comparison to strain W3110/pG97S4DhCNP-22.

Figure 14:
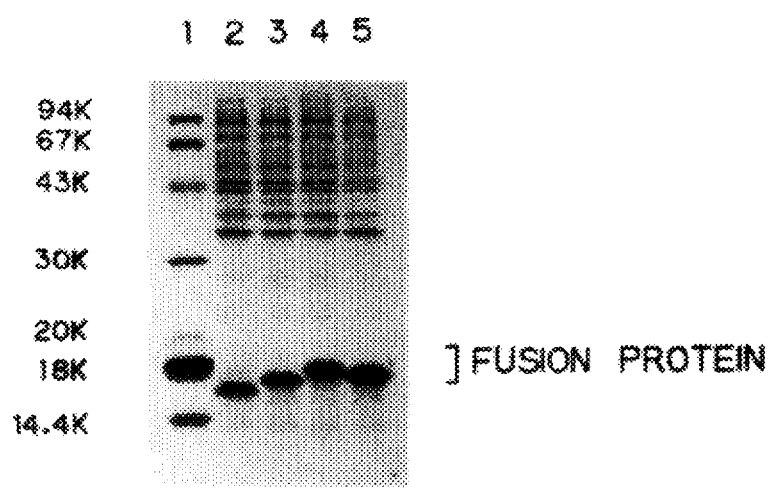
FIG. 14 is a photograph of SDS polyacrylamide gel electrophoresis indicating a result comparing the amounts of fusion proteins expressed for which the isoelectric points have been adjusted.

In particular, it was clear that a large amount of fusion protein was expressed by strain W3110/pG97S4DhCNP-22R5-2 providing an isoelectric point of 5.59 and strain W3110/pG97S4DhCNP-22R5-3 providing an isoelectric point of 6.22 in comparison to strain W3110/pG97S4DhDCNP-22 (see FIG. 14). In the case of this human CNP-22 as well, it was indicated that the isoelectric point of the fusion protein processing within the range of pI 4.9–6.9 results in improved productivity of fusion protein.

Moreover, it was also verified by the inventors of the present invention that human CNP-22 from inclusion bodies of fusion protein produced in *Escherichia coli* in this manner is efficiently released using V8 protease resulting in efficient production of human CNP-22, thereby indicating the usefulness of the present invention.

EXAMPLES

The following Examples provides a detailed explanation of the present invention.

Example 1

Construction of Expression Vector

An expression plasmid that expresses fusion protein having 1 to 10 arginine residues in the linker peptide region was constructed in the manner described below.

(A) Construction of pG97S4DhCT(G)R10

The procedure described below was performed to insert a gene coding for the amino acids of the R10 region indicated in FIG. 1 into the linker peptide coding region between a β-gal 97S4D (peptide consisting 97 amino acids of the N-terminal of β-galactosidase wherein a cysteine residue is substituted by a serine residue and four glutamic acid residues are substituted by aspartic acid residues) gene and an hCT(G) (human calcitonin precursor having 1 glycine residue at the C-terminal) gene. A construction process for pG97S4DhCT(G)R10 is indicated in FIG. 2.

First of all, pBR322 was digested with restriction enzymes to isolate the R10 region within the tetracycline-resistant gene of pBR322. 150 μg of pBR322 was digested with 200 units each of BamHI and Eco47III for 60 minutes at 37° C. in 300 μl of High buffer (50 mM Tris/HCl pH 7.5, 100 mM NaCl, 10 mM MgCl$_2$ and 1 mM dithiothreitol abbreviated as DTT).

After reaction, 30 μl of a dye solution (0.25% bromphenol blue, 0.25% xylene cyanol, 40% sucrose) was added to the reaction mixture, and 1.5% agarose are gel electrophoresis (TAE buffer solution; 40 mM Tris-acetic acid pH 8.0, 2 mM EDTA, 120 V, 2 hours) was performed. Following electrophoresis, the gel was immersed in 0.5 μg/ml of ethidium bromide solution, the 119 bp of BamHI-Eco47III fragment was cut out from the gel.

The cut out gel was then place in a dialysis tube containing TAE buffer and electrophoresed (120 V, 30 minutes) to elute the 119 bp DNA fragment from the gel. The solution in the dialysis tube was then collected followed by phenol treatment, chloroform treatment and ethanol precipitation according to commonly used methods, and the ethanol precipitate was dissolved in 40 μl of TE buffer (10 mM Tris/HCl pH 8.0, 1 mM EDTA). 2.5 μl of 10-fold concentrated Med buffer (100 mM Tris/HCl pH 7.5, 500 mM NaCl, 100 mM MgCl$_2$ and 10 mM DTT) and 10 units of HaeIII were added to 20 μl of this BamHI-Eco47III (119 bp) DNA fragment-containing solution, and digested for 2 hours at 37° C. After addition of dye solution, 15% polyacrylamide gel electrophoresis (TBE buffer; 89 mM Tris-boric acid buffer pH 8.0, 2 mM EDTA, 120 V, 90 minutes) was carried out.

And then the gel was stained in ethidium bromide solution, and the band of the HaeIII-Eco47III DNA fragment (89 bp) was cut out from the gel. This cut out gel was cut up into fine pieces and allowed to stand for 12 hours at 37° C. in 200 μl of DNA elution buffer (0.5M ammonium acetate, 1 mM EDTA pH 8.0). Phenol treatment, chloroform treatment and ethanol precipitation were then performed according to commonly used methods, and the ethanol precipitate was dissolved in 5 μl of TE buffer (10 mM Tris/HCl pH 8.0, 1 mM EDTA).

Next, 5 μg of pG97S4DhCT(G) plasmid was digested for 2 hours at 37° C. in 50 μl of TA buffer (33 mM Tris/acetic acid pH 7.9, 10 mM magnesium acetate, 0.5 mM DTT, 66 mM potassium acetate, 0.01% bovine serum albumin) with 30 units of EcoRI. Moreover, 1 μl of 25 mM dNTP consisting of dATP, dGTP, dCTP and dTTP and 4 units of T4 DNA polymerase were added to this reaction solution to fill in the cohesive ends for 5 minutes at 37° C. After the reaction, phenol treatment, chloroform treatment and ethanol precipitation were performed according to commonly used methods, and the ethanol precipitate was dissolved in 10 μl of TE buffer.

Five μl of coRI-digested and blunt ended pG97S4DhCT (G) and 5 μl of the HaeIII-Eco47III DNA fragment (89 bp) were mixed, and ligation reaction was carried out for 12 hours at 16° C. with a DNA ligation kit (Takara Shuzo). The ligation mixture was used to transform Escherichia coli W3110 according to commonly used methods, and tetracycline-resistant transformants were obtained. The plasmid structure was confirmed by restriction enzyme analysis with BspHI and BglII, and one of the transformants carring a desired structure was named W3110/pG97S4DhCT(G) R10 strain.

(B) Construction of pG97S4DhCT(G)R6

The procedure described below was performed to insert a gene coding for the amino acids of the R6 region indicated in FIG. 1 into the linker peptide-coding between β-gal 97S4D gene. The construction of pG97S4DhCT(G)R6 is shown in FIG. 2.

pBR322 was digested with a restriction enzymes in order to isolate the R6 region within the tetracycline-resistant gene of pBR322. 150 μg of pBR322 was digested with 200 units each of BamHI and Eco47III for 60 minutes at 37° C. in 300 μl of High buffer (50 mM Tris/HCl pH 7.5, 100 mM NaCl, 10 mM MgCl$_2$ and 1 mM DTT). After the reaction, 30 μl of a dye solution (0.25% bromphenol blue, 0.25% xylene cyanol, 40% sucrose) was added to the reaction mixture, and the reaction mixture was used for 1.5% agarose gel electrophoresis (TAE buffer solution; 40 mM Tris-acetic acid pH 8.0, 2 mM EDTA, 120 V, 2 hours).

After the gel electrophoresis, the gel was stained in 0.5 μg/ml of ethidium bromide solution, and the band of the BamHI-Eco47III (119 bp) DNA fragment was cut out from the gel. The cut out gel was then place in a dialysis tube containing TAE buffer and electrophoresed (120 V, 30 minutes) to elute the 119 bp DNA fragment from the gel. The solution in the dialysis tube was then collected followed by phenol treatment, chloroform treatment and ethanol precipitation according to commonly used methods, and the ethanol precipitate was dissolved in 40 μl of TE buffer (10 mM Tris/HCl pH 8.0, 1 mM EDTA).

2.5 μl of 10-fold concentrated TA buffer (330 mM Tris/HCl pH 7.9, 100 mM magnesium acetate, 5 mM DTT, 660 mM potassium acetate and 0.1% bovine serum albumin) and 10 units of BanI were added to 20 μl of this BamHI-Eco47III (119 bp)-containing solution and incubated for 2 hours at 37° C. Furthermore, 1 μl of 25 mM dNTP and 4 units of T4 DNA polymerase were added to fill in the cohesive ends for 5 minutes at 37° C. After addition of 2.5 μl of dye solution to the reaction mixture, 15% polyacrylamide gel electrophoresis (TBE buffer; 89 mM Tris-boric acid buffer pH 8.0, 2 mM EDTA, 120 V, 90 minutes) was carried out.

Following the electrophoresis, the gel was stained in ethidium bromide solution, and the band of the HaeIII-Eco47III DNA fragment (56 bp) was cut out from the gel. This cut out gel was cut up into fine pieces and allowed to stand for 12 hours at 37° C. in 200 μl of DNA elution buffer (0.5M ammonium acetate, 1 mM EDTA pH 8.0). Phenol treatment, chloroform treatment and ethanol precipitation were then performed according to commonly used methods, and the ethanol precipitate was dissolved in 5 μl of TE buffer (10 mM Tris/HCl pH 8.0, 1 mM EDTA).

5 μg of pG97S4DhCT(G) plasmid was digested with 30 units of EcoRI for 2 hours at 37° C. in 50 μl of TA buffer. Moreover, 1 μl of 25 mM dNTP and 4 units of T4 DNA polymerase were added to this reaction solution fill in the cohesive ends for 5 minutes at 37° C. After the reaction, phenol treatment, chloroform treatment and ethanol precipitation were performed according to commonly used methods, and the ethanol precipitate was dissolved in 10 μl of TE buffer.

5 μl of EcoRI-digested and blunt ended pG97S4DhCT(G) and 5 μl of the BanI-Eco47III DNA fragment (56 bp) were mixed, and ligation reaction was performed for 12 hours at 16° C. with a DNA ligation kit (Takara Shuzo). The reaction mixture was used to transform *Escherichia coli* W3110 according to commonly used methods, and tetracycline-resistant transformants were obtained. The plasmid structure was confirmed by restriction enzyme analysis with BspHI and BglII, and one of the transformants carring a desired structure was named W3110/pG97S$_4$DhCT(G)R6.

(C) Construction of pG97S4DhCT(G)R8

Figure 3:
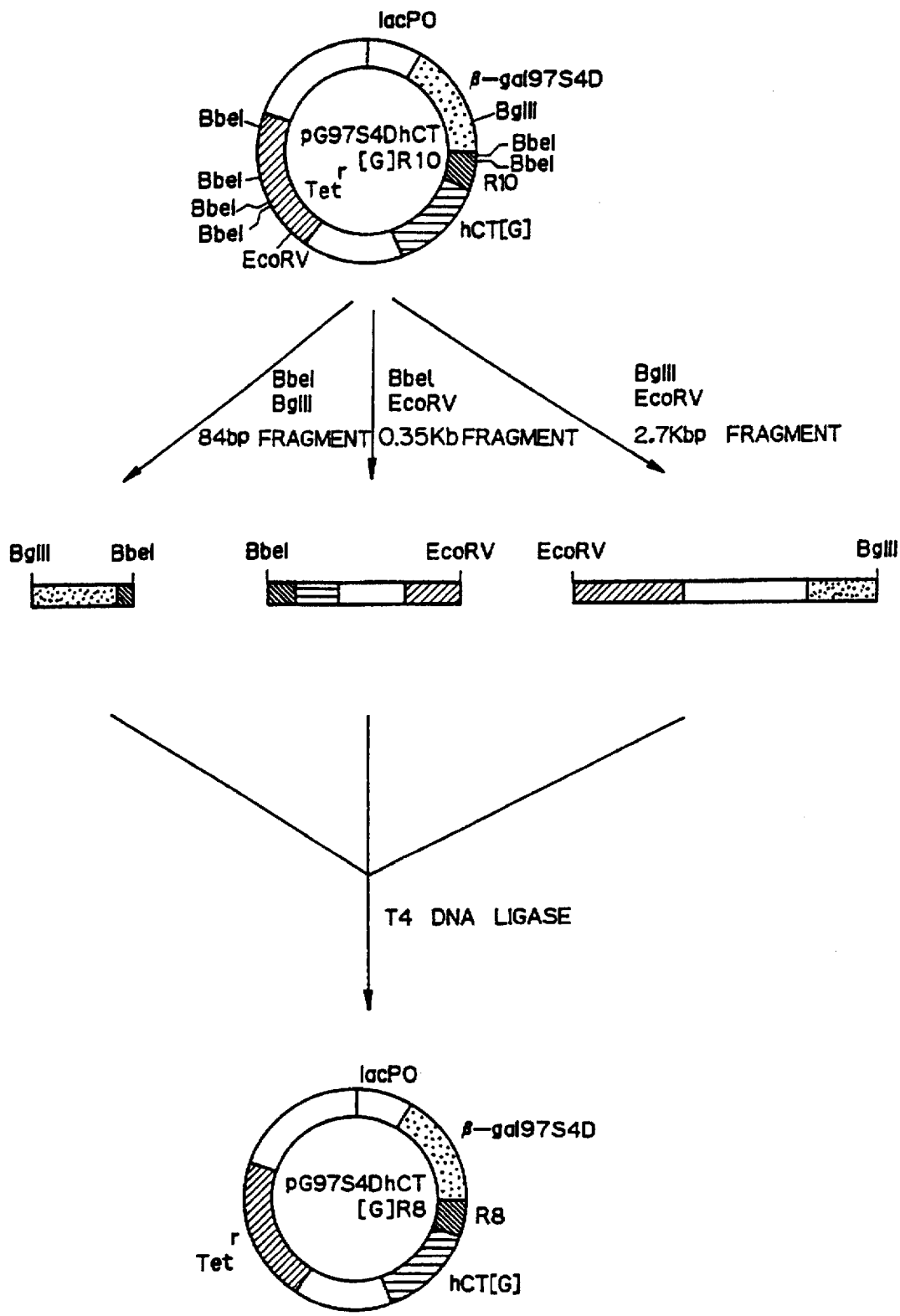
FIG. 3 indicates a process for construction of plasmid pG97S4DhCT(G)R8.

The procedure described below was performed to insert a gene coding for the amino acids of the R8 region indicated in FIG. 1 into the linker peptide cording region between β-gal 97S4D gene and an hCT(G) gene. The construction of pG97S4DhCT(G)R8 is indicated in FIG. 3.

Three tubes were prepared by placing 10 μg of pG97S4DhCT(G)R10 into each tube containing 50 μl of High buffer. 20 units of BbeI and BglII, BbeI and EcoRV, and BglII and EcoRV were respectively added in the three tubes. After allowing to react for 2 hours at 37° C., 1.5% agarose gel electrophoresis was performed, and the BbeI-BglII (89 bp), BbeI-EcoRV (353 bp) and BglII-EcoRV (2.7 Kb) and bands were cut out from the gel, and electrophoresis was carried out.

Phenol treatment, chloroform treatment and ethanol precipitation were then performed according to commonly used methods, after which the ethanol precipitate was dissolved in 5 μl of TE buffer. The three DNA fragments obtained in this manner were mixed and ligated for 12 hours at 16° C. using a DNA ligation kit. The ligation mixture was used to transform *Escherichia coli* W3110 according to commonly used methods, and tetracycline-resistant transformants were obtained. The plasmid structure was confirmed by restriction enzyme analysis, and one of the transformant was named *E. coli* W3110/pG97S4DhCT(G)R8 strain.

(D) Construction of pG97S4DhCT(G)R1, pG97S4DhCT(G) R3,
    pG97S4DhCT(G)R4 and pG97S4DhCT(G)R5

The procedure described below was performed to insert gene coding for the amino acids of the R1, R3, R4 or R5 region indicated in FIG. 1 into the linker peptide-coding region between a β-gal 97S4D gene and an hCT(G) gene.

Figure 4:
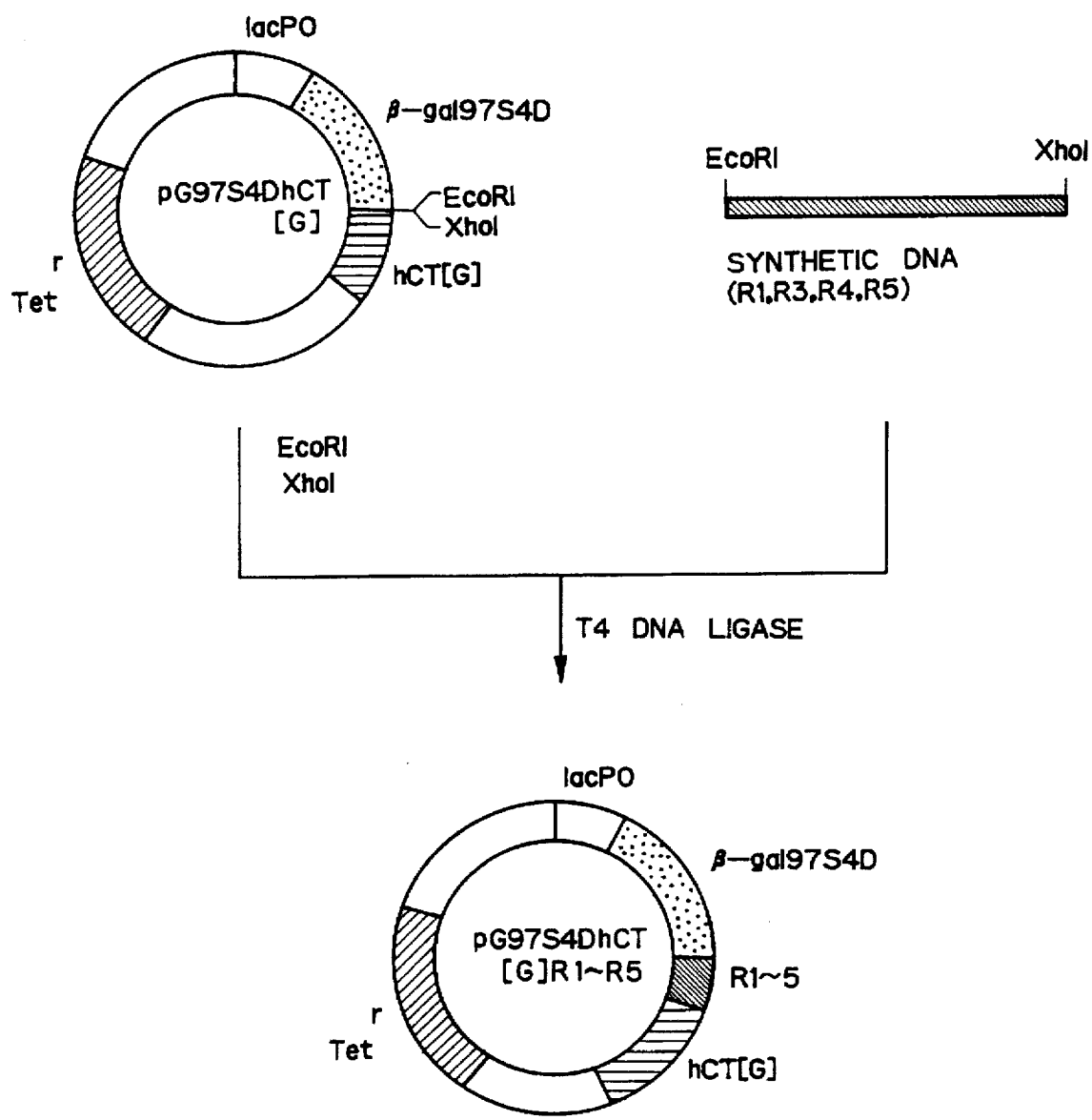
FIG. 4 indicates a process for construction of plasmids pG97S4DhCT(G)R1–R5.

The construction of pG97S4DhCT(G)R1, pG97S4DhCT(G)R3, pG97S4DhCT(G)R4 and pG97S4DhCT(G)R5 is indicated in FIG. 4.

25 μg of pG97S4DhCT(G) was digested with 30 units of each of EcoRI and XhoI in 50 μl of High buffer for 2 hours at 37° C. Following the reaction, 1% agarose gel electrophoresis was performed and the 3.2 Kb DNA fragment was isolated from the gel by electrophoresis. 100 pmole each of this DNA fragment and the chemically synthesized oligonucleotide indicated in FIG. 5 were mixed and ligated. The ligation mixture was used to transform *Escherichia coli* W3110 according to commonly used method, and tetracycline-resistant transformants were obtained.

After analyzing the plasmid of the transformed strain by gel electrophoresis after cleavage with restriction enzymes, *E. coli* W3110/pG97S4DhCT(G)R1 strain, W3110/pG97S4DhCT(G)R3 strain, W3110/pG97S4DhCT(G)R4 strain and W3110/pG97S4DhCT(G)R5 strain were obtained.

As indicated above, 7 types of plasmids were constructed wherein a portion of a tetracycline-resistant gene was inserted into the EcoRI cleavage site or EcoRI-XhoI cleavage site of pG97S4DhCT(G). As these inserted genes contain from 1 to a maximum of 10 codons corresponding to the basic amino acid arginine, the charges differ between the chimeric proteins thus resulting in the production of fusion proteins having different isoelectric points. The structures of the fusion proteins produced are indicated in FIG. 6.

Example 2

Expression of hCT(G) Fusion Protein

In order to examine the relationship between the isoelectric points of fusion proteins produced in microorganisms and their productivity, the microorganisms were cultured and the productivity of fusion protein per number of cells was determined by using SDS polyacrylamide gel electrophoresis.

The prepared microorganism was cultured in a flask for 12 hours at 37° C. in 500 ml of SB medium (0.5% glycerine, 2.4% yeast extract, 1.2% tryptone, 100 mM potassium hydrogen phosphate pH 7.5 and tetracycline (10 μg/ml)). Following culturing, the turbidity of the culture broth was measured with a spectrophotometer ($OD_{660}$), and the culture broth was removed so that the value of [$OD_{660}$ value×culture volume (ml)] became 5, followed by centrifugation for 5 minutes at 12000 rpm to separate the microbial cells.

1 ml of SDS sample buffer (63 mM Tris-HCl pH 6.8, 10% glycerine, 10% SDS, 5% 2-mercaptoethanol and 12.5 mg/L bromphenol blue) was added to the cell precipitate followed by heating for 5 minutes at 95° C. to obtain the sample for SDS polyacrylamide gel electrophoresis. SDS-16% polyacrylamide gel electrophoresis (TEFCO) was performed using 5 μl of the above-mentioned sample under the conditions of 18 mA for 90 minutes. Following the electrophoresis, the gel was dyed with a dye solution (10% acetic acid, 40% methanol and 2 g/L of Coomassie brilliant blue R-250) and the productivity per number of cells of the hCT(G) fusion protein produced by each strain were compared. The results of electrophoresis are indicated in FIG. 7.

Figure 7:
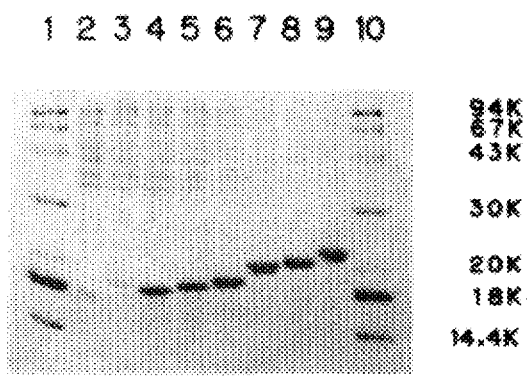
FIG. 7 is a photograph of SDS polyacrylamide gel electrophoresis indicating the states of expression of the fusion proteins from each of the expression plasmids.

As is clear from FIG. 7, strain W3110/pG97S4DhCT(G) providing an isoelectric point of 4.43 produced only an extremely small amount of fusion protein, while strain W3110/pG97S4DhCT(G)R1 providing an isoelectric point of 4.70 only produced a small amount of fusion protein. It was also clear that the other strains produced a large amount of fusion protein in cells. Thus, these results indicated that productivity of fusion protein as well as the amount of its inclusion bodies that are formed becomes poor when the isoelectric point of the fusion protein is in the vicinity of 4.5–4.7.

Next, a study was conducted on the productivity of fusion protein and the efficiency at which hCT(G) is released from fusion protein using V8 protease under conditions of large volume culturing by performing large volume culturing and production in 30 liter culturing tanks using strains W3110/pG97S4DhCT(G)R3, W3110/pG97S4DhCT(G)R4, W3110/pG97S4DhCT(G)R5, W3110/pG97S4DhCT(G)R6, W3110/pG97S4DhCT(G)R8 and W3110/pG97S4DhCT(G)R10.

Example 3

Productivity of Fusion Protein Under Large Volume Culturing Conditions and Release Of hCT(G) from Fusion Protein using V8 Protease The following experiment was carried out to study the productivity of fusion proteins under large volume culturing conditions and the efficiency of release of hCT(G) from various hCT(G) fusion proteins by V8 protease.

Six high expression strains (W3110/pG97S4DhCT(G)R3, W3110/pG97S4DhCT(G)R4, W3110/pG97S4DhCT(G)R5, W3110/pG97S4DhCT(G)R6, W3110/pG97S4DhCT(G)R8 and W3110/pG97S4DhCT(G)R10), in which formation of inclusion bodies was observed in flask cultures using the above-mentioned SB medium, were cultured in 30 liter culturing tanks.

The medium contained 4 g/L of yeast extract, 4 of potassium dihydrogen phosphate, 4 g/L of dipotassium hydrogen phosphate, 2.7 g/L of sodium hydrogen phosphate, 1.2 g/L of ammonium sulfate, 0.2 g/L of ammonium chloride, 2.0 g/L of L-methionine, 2.0 g/L of $MgSO_4 \cdot 7H_2O$, 40 mg/L of $FeSO_4 \cdot 7H_2O$, 40 mg/L of $CaCl_2 \cdot 2H_2O$, 10 mg/L of $AlCl_3 \cdot 6H_2O$, 4 mg/L of $CoCl_2 \cdot 6H_2O$, 2 mg/L of $ZnSO_4 \cdot 7H_2O$, 2 mg/L of $Na_2MoO_4 \cdot 2H_2O$, 1.0 mg/L of $CuCl_2 \cdot 2H_2O$, 0.5 mg/L of $H_3BO_3$ and 10 mg/L of $MnSO_4 \cdot nH_2O$, using glucose (2%) for the carbon source in the initial phase of culturing, and using glycerine (8%) as the carbon source after consumption of glucose. The results of the final attained bacterial concentration are indicated in Table 1.

TABLE 1

| Strain | Final Bacterial Concentration ($OD_{660}$) (a) | Amount of Inclusions per Bacteria (Relative Value) (b) | Total Amount of Inclusion Bodies (Relative Value) (a × b) |
| --- | --- | --- | --- |
| W3110/pG97S4Dh CT(G)R10 | 53 | 116 | 6148 |
| W3110/pG97S4Dh CT(G)R8 | 120 | 113 | 13560 |
| W3110/pG97S4Dh CT(G)R6 | 110 | 106 | 11660 |
| W3110/pG97S4Dh CT(G)R5 | 105 | 100 | 10500 |
| W3110/pG97S4Dh CT(G)R4 | 94 | 100 | 9400 |
| W3110/pG97S4Dh CT(G)R3 | 106 | 96 | 10176 |

As is clear from Table 1, strain W3110/pG97S4DhCT(G)R10 demonstrated remarkably poor growth in comparison to the other strains, reaching a final attained bacterial concentration roughly only half that of the other strains. In addition, although the isoelectric point of the fusion protein produced by strain W3110/pG97S4DhCT(G)R10 was slightly alkaline at 7.85, and there was an increase in the productivity of fusion protein per cell, perhaps due to the rapid formation of inclusion bodies or the isoelectric point of the fusion protein being slightly alkaline, cell growth was inhibited which resulted in a low cell concentration.

Thus, based on the results of these studies, it was verified for the first time by the inventors of the present invention that in order to produce fusion protein as inclusion bodies in *Escherichia coli* both stably and in large amounts, it is important to maintain the isoelectric point of the fusion protein in the acidic region between 4.9 and 6.9. In addition, following the SDS polyacrylamide gel electrophoresis and dyeing proteins, the amount of fusion protein produced per cells was determined with a gel scanner. Those results are indicated in Table 1 as the amount of inclusion bodies per cells (relative value).

When the amount of fusion protein per cells was taken to be 100 for strain W3110/pG97S4DhCT(G)R4, each of the strains produced 96–116 inclusions. The total amount of inclusion bodies per culture liquid was 6,148 for strain W3110/pG97S4DhCT(G)R10 strain and 13560 for strain W3110/pG97S4DhCT(G)R8, indicating a difference of nearly a factor of 2. Although strain W3110/pG97S4DhCT(G)R8 demonstrated the largest total amount of inclusion bodies per culture broth, a cleavage reaction took place by V8 protease from fusion protein during production of hCT, with the efficiency of the cleavage reaction by V8 protease from fusion protein being closely involved with the yield of the production process.

As such, a study was conducted of the efficiency of the clevage reaction by V8 protease using the inclusion bodies obtained. After culturing using the above-mentioned 30 liter culturing tanks, 1000 ml of culture broth was removed followed by homogenization of the cells using a high-pressure homogenizer (Manton Gaulin Laboratory Homogenizer 15M-8TA) at 600 $Kg/cm^2$. The precipitate containing the inclusion bodies was collected by centrifugation for 30 minutes at 7000 rpm. After addition of deionized water to the precipitate fraction to make the amount of the fraction equal to the initial volume, the suspension was centrifuged again to wash the precipitate.

After repeating the washing procedure one more time, the finally obtained precipitate was suspended with deionized water so that the $OD_{660}$ value became 800, and used in V8 protease cleavage reaction as described below. After removing 0.6 ml of suspension, adding 75 μl of 1M Tris-HCl (pH 8.0), 7.5 μl of 0.5 MEDTA (pH 8.0) 540 mg of urea and 185 μl of 100 mM DTT to this suspension, and allowing to stand for 10 minutes at 30° C., deionized water was added to bring the final volume to 3.7 ml. After preheating for 10 minutes at 30° C., 7 μl of V8 protease (1 mg/ml) was added and allowed to react for 1 hour.

Quantitative determination of the cleaved hCT(G) was performed by high performance liquid chromatography (HPLC) using a YMC Packed column A-302 (0.46 cm×15 cm, Yamamura Chemical Research). Elution was performed with a linear concentration gradient using 0.1% trifluoroacetic acid (TFA) and 0.1% TFA/50% acetonitrile. As a result, it was verified that the efficiency of cleavage of hCT(G) from fusion protein differed greatly depending on the hCT(G) fusion protein.

Strain W3110/pG97S4DhCT(G)R4 demonstrated the highest cleavage efficiency of 97%, while strain W3110/pG97S4DhCT(G)R5 demonstrated the lowest cleavage efficiency of 7%. There was no correlation whatsoever between this cleavage efficiency and the final bacterial concentration. In addition, there was also no correlation observed for the number of basic amino acid residues of the linker peptide inserted into the fusion protein. On the contrary, the cleavage efficiency was believed to be influenced by the amino acid sequence of the region of the cleavage recognition site for V8 protease. In any case, as strain W3110/pG97S4DhCT(G)R4 demonstrated the largest amount of recovery of hCT(G), conversion from human calcitonin precursor to human calcitonin by an amidation enzyme was performed using this bacterial strain.

Example 4

Purification of hCT(G) Precursor and Conversion to Human Calcitonin by an Amidation Enzyme After culturing strain W3110/pG97S4DhCT(G)R4 in a 20 liter culturing tank in the manner described above, a suspension of inclusion bodies of fusion protein was obtained according to the method described above. After removing 6 ml of this suspension of inclusion bodies, adding 750 μl of 1M Tris-HCl (pH 8.0), 75 μl of 0.5M EDTA (pH 8.0), 5.4 g of urea and 17 mg of DTT, and allowing to stand for 10 minutes, deionized water was added to bring the final volume to 37 ml. Next, 40 µl of V8 protease (1 mg/ml) was added to treat the suspension for 90 minutes at 37° C.

After that diluting the reaction solution by a factor of 2 with deionized water, acetic acid was added after allowing to stand for 30 minutes to bring the pH to 4.6. The β-gal97S4D of the protective peptide precipitated as a result of lowering the pH to 4.6 while hCT(G) remained in the supernatant fraction. The supernatant fraction was separated by centrifuging for 15 minutes after which this supernatant fraction was applied to a column of SP Sepharose (Tosoh) equilibrated with 10 mM ammonium acetate (pH 4.6) followed by column chromatography. hCT(G) eluted in stages with 40 mM ammonium acetate (pH 6.5). Roughly 0.4 g of hCT(G) were obtained per liter of culture liquid.

Figure 8:
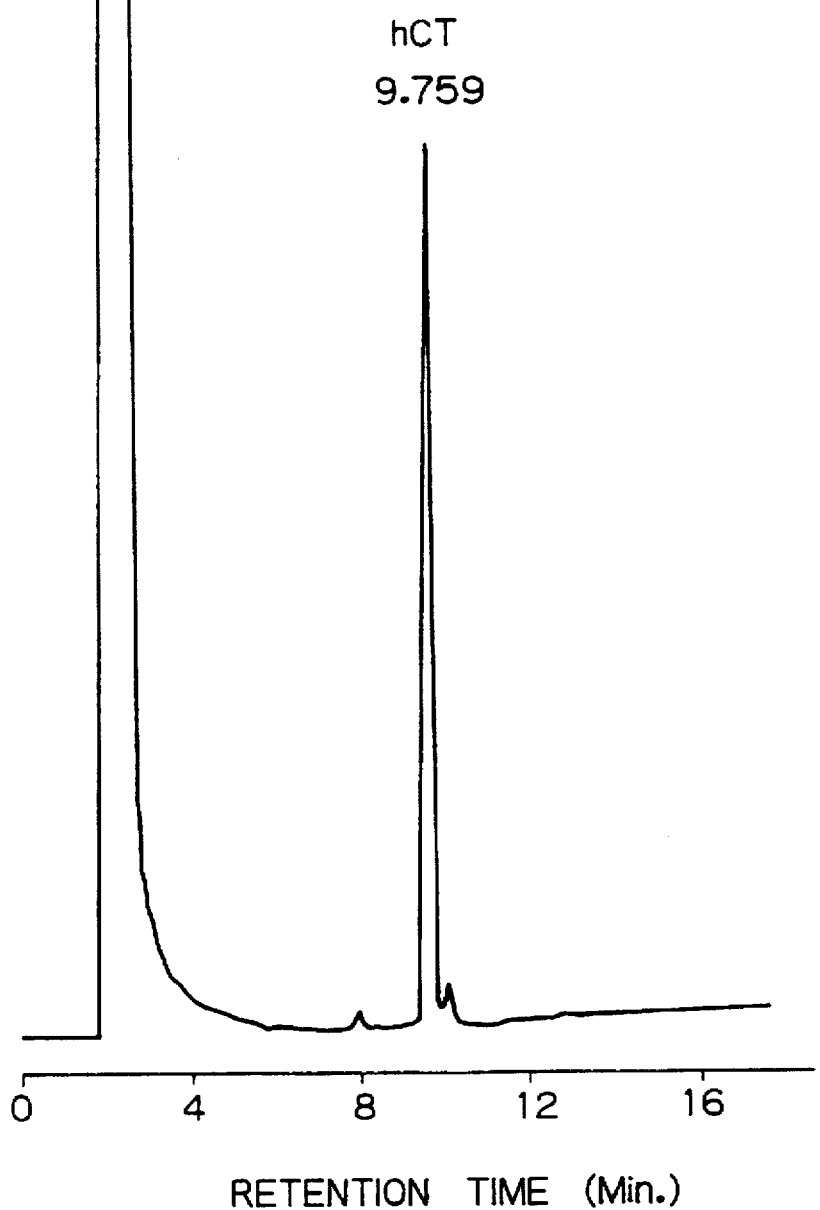
FIG. 8 indicates the results of high performance liquid chromatography of human calcitonin obtained by the method of the present invention.

Human calcitonin was able to be produced with good efficiency by reacting the hCT(G) obtained in the manner above with amidation enzyme according to the method described in Unexamined Patent Publication No. 2-190193. Following the amidation reaction, high performance liquid chromatography was performed using YMC packed column A-302 (Yamamura Chemical Research), the results of which are indicated in FIG. 8. Under these elution conditions, human calcitonin eluted at a retention time of 9.7 minutes, and as is clear from this figure, it is possible to obtain human calcitonin having a high purity in extremely high yield.

Example 5

Preparation of Human CNP-22 Gene

A gene coding for human CNP-22, in which a glutamic acid residue, the severing site of V8 protease, is added to the N terminal, was prepared as indicated below using in vitro DNA amplification (PCR).

pUCCNP1 plasmid was used for the template DNA. 1.57 µg of pUCCNP1 was digested for 60 minutes at 37° C. in 157 µl of K buffer (20 mM Tris/HCl pH 8.5, 100 mM KCl and 1 mM dithreitol abbreviated as DTT) with 12 units of EcoRI to cleave the plasmid. Phenol treatment, 2-butanol treatment and ethanol precipitation were performed on the reaction solution according to commonly used methods, and EcoRI-digested DNA fragment was dissolved in 157 µl of TE buffer (10 mM Tris/HCl pH 8.0 and 1 mM EDTA).

The designs of the primers used for the PCR reaction are indicated in FIG. 9. Primer 1 (SEQ ID NO 11) was designed so that a glutamic acid residue that is cleaved by V8 protease is added to the N terminal of human CNP-22, and ECORI and XhoI restriction enzyme cleavage sites are provided further upstream, while primer 2 (SEQ ID NO 12) was designed so that a SalI restriction enzyme cleavage site is provided immediately after the human CNP-22 gene. These primers were synthesized using a DNA synthesizer (Applied Biosystems, Model 380A). Following synthesis, electrophoresis was performed using 20% polyacrylamide gel containing 8M urea and the DNA fragments of a length corresponding to the primers were released to produce each of the primers.

After allowing 10 ng of pUCCNP1 cleaved with the above-mentioned EcoRI and 100 µl of reaction solution (10 mM Tris/HCl pH 8.3, 50 mM KCl, 1.5 mM MgCl₂, 0.1% gelatin and 200 µM each of dGTP, dATP, dTTP and dCTP) containing primer (1 pmol each) to stand for 5 minutes at 95° C., the solutions were rapidly cooled with ice. 0.5 units of Taq DNA polymerase (Ampli-Taq, Takara Shuzo) were then added followed by the addition of mineral oil to carry out the PCR reaction using a thermal reactor (Hybaid).

The QCR reaction was repeated for 30 cycles, with a single cycle consisting of consecutive reactions consisting of thermal denaturation (92° C., 1 minute), annealing (55° C., 2 minutes) and DNA elongation (72° C., 3 minutes). DNA elongation reaction of the final cycle was further performed for an additional 7 minutes. Following the reaction, after addition of TE buffer to bring to a volume of 400 µl, the entire volume was placed in a SUPREC-02 (Takara Shuzo) and centrifuged for 8 minutes at 2,000 G. The filtrate was removed and TE buffer was again added to bring the amount of liquid up to 400 µl. The centrifugation procedure was then performed again in the same manner. The PCR reaction solution remaining in the filter cup was brought to a volume of 40 µl with TE buffer.

5 µl of 10 times-concentrated High buffer (500 mM Tris/HCl pH 7.5, 1M NaCl, 100 mM MgCl₂ and 10 mM DTT), 36 units of EcoRI and 60 units of SalI were added to the 40 µl of PCR reaction mixture. After bringing the total volume to 50 µl with water, the reaction was allowed to proceed for 60 minutes at 37° C. Following the reaction, phenol treatment, 2-butanol treatment and ethanol precipitation were performed, and the precipitate was finally dissolved in TE buffer to prepare the human CNP-22 gene having EcoRI and SalI cohesive ends on both ends of the gene.

Example 6

(a): Construction of Expression Plasmid pG97S4DhCNP-220

The PCR product of the CNP-22 gene indicated in FIG. 10 was inserted into plasmid pG97S4DhCT(GRRR) containing the β-gal97S4D (peptide consisting of 97 amino acids of the N-terminal of β-galactosidase, in which a cysteine residue is substituted by a serine residue, and four glutamic acid residues are substituted by aspartic acid residues) gene. That construction process is described below.

10 µg of pG97S4DhCT(GRRR) was digested with 36 units of EcoRI and 60 units of SalI in 70 µl of High buffer for 6 minutes at 37° C. Following the reaction, 1.0% agarose gel electrophoresis was performed according to commonly used methods, and a band of 3.2 Kb EcoRI-SalI fragment was cut out from the gel. The DNA fragment in the gel slice was extracted using a SUPREC-01 (Takara Shuzo) microcentrifuge tube followed by purification by phenol treatment, chloroform treatment and ethanol precipitation.

Next, 5 µl each of this EcoRI-SalI DNA fragment and the PCR product human CNP-22 gene fragment (EcoRI-SalI DNA fragment) were mixed, and ligated with a DNA ligation kit (Takara Shuzo). The ligation mixture was used to transform *Escherichia coli* W3110, and one of the transformants was named W3110/pG97S4DhCNP-22 strain.

Example 6

(b): Construction of Expression Plasmid pG97S4DhCNP-22R3-2 and pG97S4DhCNP-22R5-2

Figure 12:
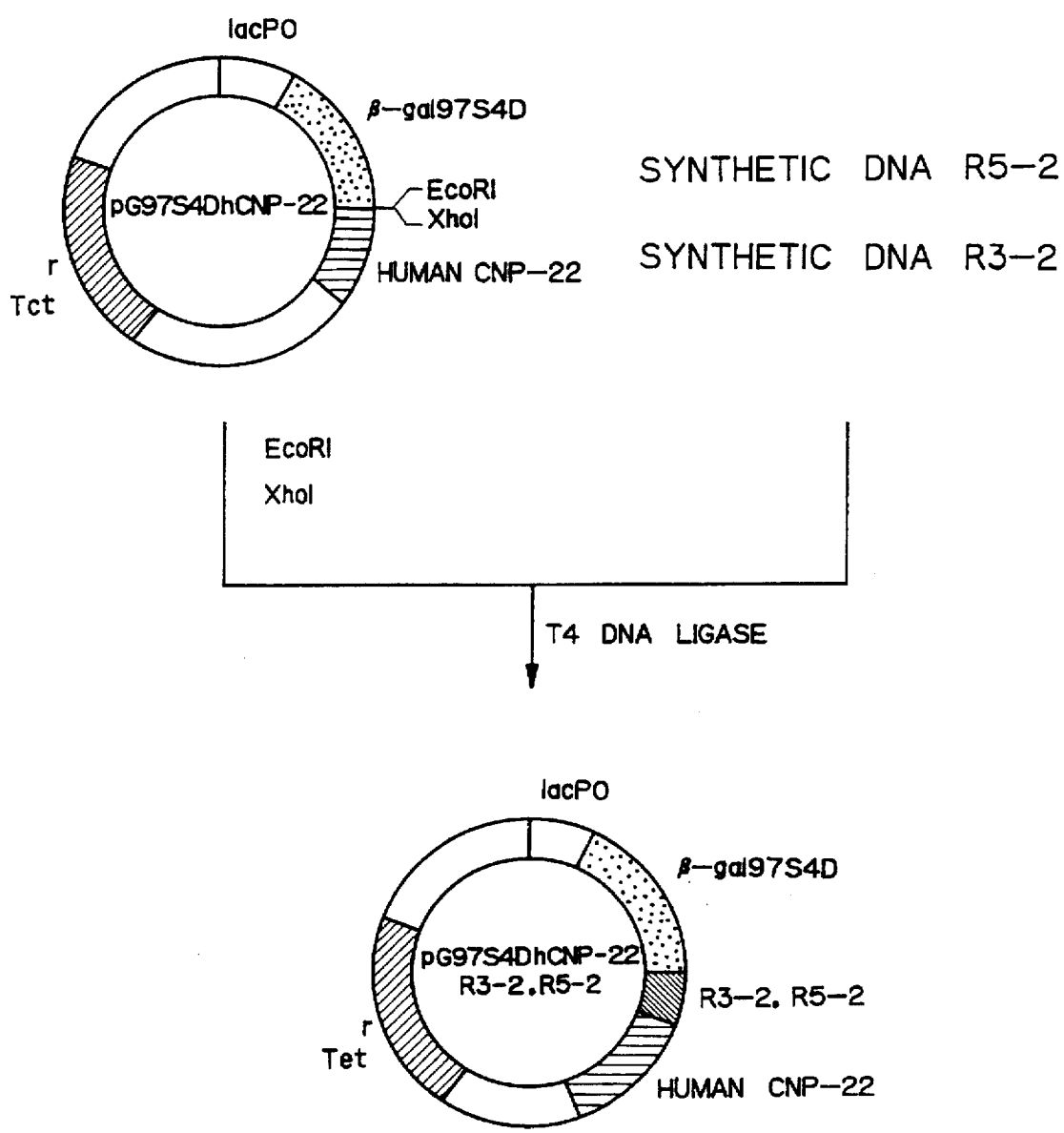
FIG. 12 indicates a process for construction of plasmids pG97S4DhCNP-22R3-2 and pG97S4DhCNP-22R5-2.

The following procedure was performed to insert a linker peptide gene coding for the amino acid sequence of R3-2 or R5-2 indicated in FIG. 11 into the linker peptide-coding region between β-gal197S4D gene and human CNP-22 gene. The construction of pG97S4DhCNP-22R3-2 and pG97S4DhCNP-22R5-2 is indicated in FIG. 12.

3 µg of pG97S4DhCNP-22 was digested with 10 units each of EcoRI and XhoI for 2 hours at 37° C. in 50 µl of High buffer. Following the reaction, 1% agarose gel electrophoresis was performed and a 3.2 kb DNA fragment was isolated from the gel by electroelution. Ligation was performed on this DNA fragment and 20 pmol of chemically synthesized oligonucleotide coding for the R3-2 and R5-2 sequences using a ligation kit (Takara Shuzo). The ligation mixture was used to transform *Escherichia coli* W3110. Following isolation of the plasmid from the tetracycline-resistant transformed strain, structural analysis of the plasmid was performed using restriction enzymes to obtain the target W3110/pG97S4DhCNP-22R3-2 and W3110/pG97S4DhCNP-22R5-2.

Example 6

(c): Construction of pG97S4DhCNP-22R5-3

Figure 13:
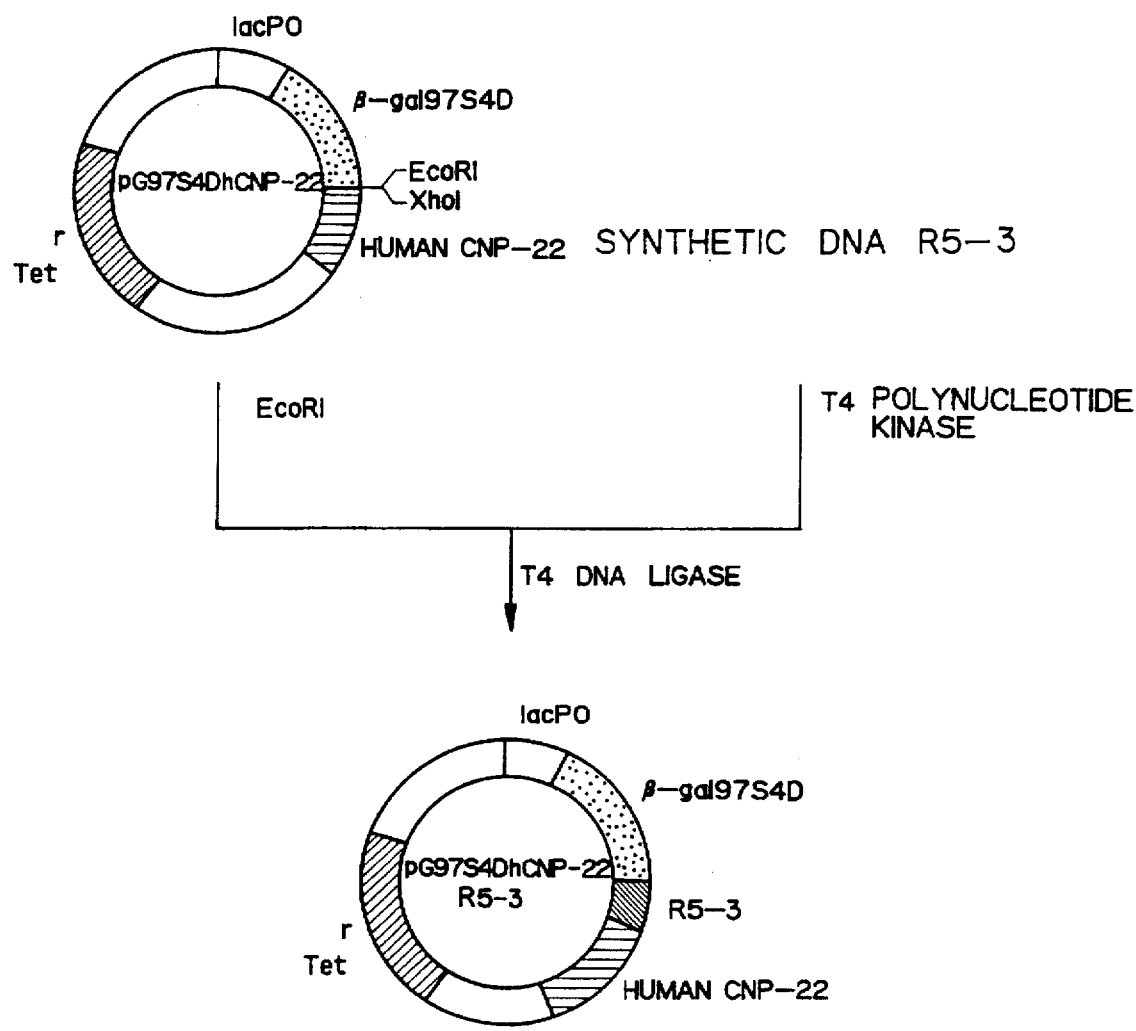
FIG. 13 indicates a process for construction of plasmid pG97S4DhCNP-22R5-3.

The following procedure was performed to insert a linker peptide gene coding for the amino acid sequence of R5-3 indicated in FIG. 11 into the pG97S4DhCNP-22 plasmid. The construction of pG97S4DhCNP-22R5-3 is indicated in FIG. 13. 3 μg of pG97S4DhCNP-22 was digested with 10 units of EcoRI for 2 hours at 37° C. in 50 μl of High buffer. After digestion, 0.5 units of alkaline phosphatase was added to dephosphorylate the 5' terminal for 1 hour at 37° C. And then, phenol treatment was performed to inactivate alkaline phosphatase. 1% agarose gel electrophoresis was carried out, and the 3.2 Kb DNA fragment was isolated from the gel by electrophoresis. Next, 3 μg of chemically synthesized oligonucleotide coding for the amino acid sequence of R5-3 was treated with 20 units of T4 polynucleotide kinase in 100 μl of T4 polynucleotide kinase reaction solution (50 mM Tris/HCl pH 8.0, 10 mM $MgCl_2$, 10 mM 2-mercaptoethanol and 1 mM ATP) to phosphorylate the 5' end for 1 hour at 37° C.

Ligation was then performed on 2 μl of this phosphorylated oligonucleotide and the above-mentioned EcoRI-cleaved, alkaline phosphatase-treated pG97S4DhCNP-22. The ligation mixture was used to transform *Escherichia coli* W3110, and tetracycline-resistant transformants were obtained. The plasmids were analyzed by restriction enzymes, and W3110/pG97S4DhCNP-22R5-3 was obtained.

Example 7

Expression of Human CNP-22 Fusion Protein

In order to examine the relationship between the isoelectric points of fusion proteins expressed in microbial cells and productivity, microorganisms were cultured and the productivity of fusion protein per number of cells was investigated using SDS polyacrylamide gel electrophoresis.

*Escherichia coli* strains were cultured in flasks for 12 hours at 37° C. in 500 ml of Nu1 medium (0.4 g/L of yeast extract, 4 g/L of potassium dihydrogen phosphate, 4 g/L of dipotassim hydrogen phosphate, 2.7 g/L of disodium hydrogen phosphate, 1.2 g/L of ammonium sulfate, 0.2 g/L of ammonium chloride, 0.8% glycerine, 2 g/L of magnesium sulfate and 10 mg/L of tetracycline).

Following the culturing, the turbidity ($OD_{660}$) of the culture broth was measured with a spectrophotometer and culture broth was adjusted to the value of ($OD_{660}$ value× culture volume (ml)) became 5, and centrifugation was carried out for 5 minutes at 12000 rpm to separate the microbial cells. 1 ml of SDS sample buffer (63 mM Tris/HCl pH 6.8, 10% glycerine, 10% SDS, 5% 2-mercaptoethanol and 12.5 mg/L of bromphenol blue) was added to these cell precipitate and heated for 5 minutes at 95° C. to obtain the sample for SDS polyacrylamide gel electrophoresis.

SDS-15% polyacrylamide gel electrophoresis (TEFCO) was performed using 5 μl of the above-mentioned sample under the conditions of 18 mA for 90 minutes. Following the electrophoresis, the gel was stained in a dye solution (10% acetic acid, 40% methanol and 2 g/L of Coomassie brilliant blue R-250) and the productivity per cell of human CNP-22 fusion protein produced in each strain was compared. The results of electrophoresis are indicated in FIG. 14.

As as indicated in FIG. 14, it is clear that when strain W3110/pG97S4DhCNP-22 providing an isoelectric point of 4.56 is compared with the other strains (W3110/pG97S4DhCNP-22R3-2 providing an isoelectric point of 4.95, W3110/pG97S4DhCNP-22R5-2 providing an isoelectric point of 6.22 and W3110/pG97S4DhCNP-22R5-3 providing an isoelectric point of 5.59), strains W3110/pG97S4DhCNP-22R3-2, W3110/pG97S4DhCNP-22R5-2 and W3110/pG97S4DhCNP-22R5-3 demonstrated greater productivity of fusion protein than strain W3110/pG97S4DhCNP-22.

It was indicated in particular that strains W3110/pG97S4DhCNP-22R5-2 and W3110/pG97S4DhCNP-22R5-3 expressed a large amount of fusion protein. Thus, it was verified in this Example as well that adjusting the isoelectric point of the fusion protein within the range of 4.9–6.9 results in increased productivity of fusion protein.

Example 8

Release of Human CNP-22 from Fusion Protein by V8 Protease

The following experiment was conducted to examine the efficiency of release of human CNP-22 from fusion protein using V8 protease.

After culturing strains W3110/pG97S4DhCNP-22R3-2, W3110/pG97S4DhCNP-22R5-2 and W3110/pG97S4DhCNP-22R5-3 in the above-mentioned Nu1 medium, 400 ml of the culture broth was harvested and homogenized by a high-pressure homogenizer (Manton Gaulin Laboratory Homogenizer 15M-8TA) at 600 $Kg/cm^2$.

A precipitate containing the inclusion bodies was collected by centrifugation for 30 minutes at 7000 rpm. 400 ml of buffer A (50 mM Tris/HCl pH 8.0, 2 mM EDTA and 1% Triton X-100) was added to the resulting precipitate fraction, and the precipitate was washed by centrifuging again after suspending. This precipitation procedure was performed twice using buffer A and once using deionized water. After suspending the finally obtained precipitate in deionized water so that the $OD_{660}$ value became 100, the fusion protein was cleaved by V8 protease using the method indicated below.

6 μl of 1M Tris/HCl (pH 8.0), 0.6 μl of 0.5M EDTA, 36 mg of urea and 3 μl of 1M DTT were added to 60 μl of the inclusion body suspension and then allowed to stand for 10 minutes. After standing, deionized water was added to bring the final volume to 300 μl. 1 μl of V8 protease (1 mg/ml) was then added and a cleavage reaction was allowed to proceed for 1 hour at 30° C. Quantitative determination of the human CNP-22 cleaved from the fusion protein was performed by high performance liquid chromatography (HPLC) using a YMC Packed column A-302 (2.46 cm×15 cm, Yamamura Chemical Research).

The V8 protease reaction solution was diluted by a factor of 20 with 2M urea and 6% acetic acid solution followed by HPLC analysis using 20 μl of that diluted solution. HPLC elution was performed with a linear concentration gradient using 0.1% trifluoroacetic acid (TFA), 0.1% TFA and 50% acetonitrile. The elution patterns before and after cleavage vering of β-gal97S4DhCNP-22R5-3 fusion protein by V8 protease are indicated in FIG. 15 and FIG. 16, respectively.

Figure 15:
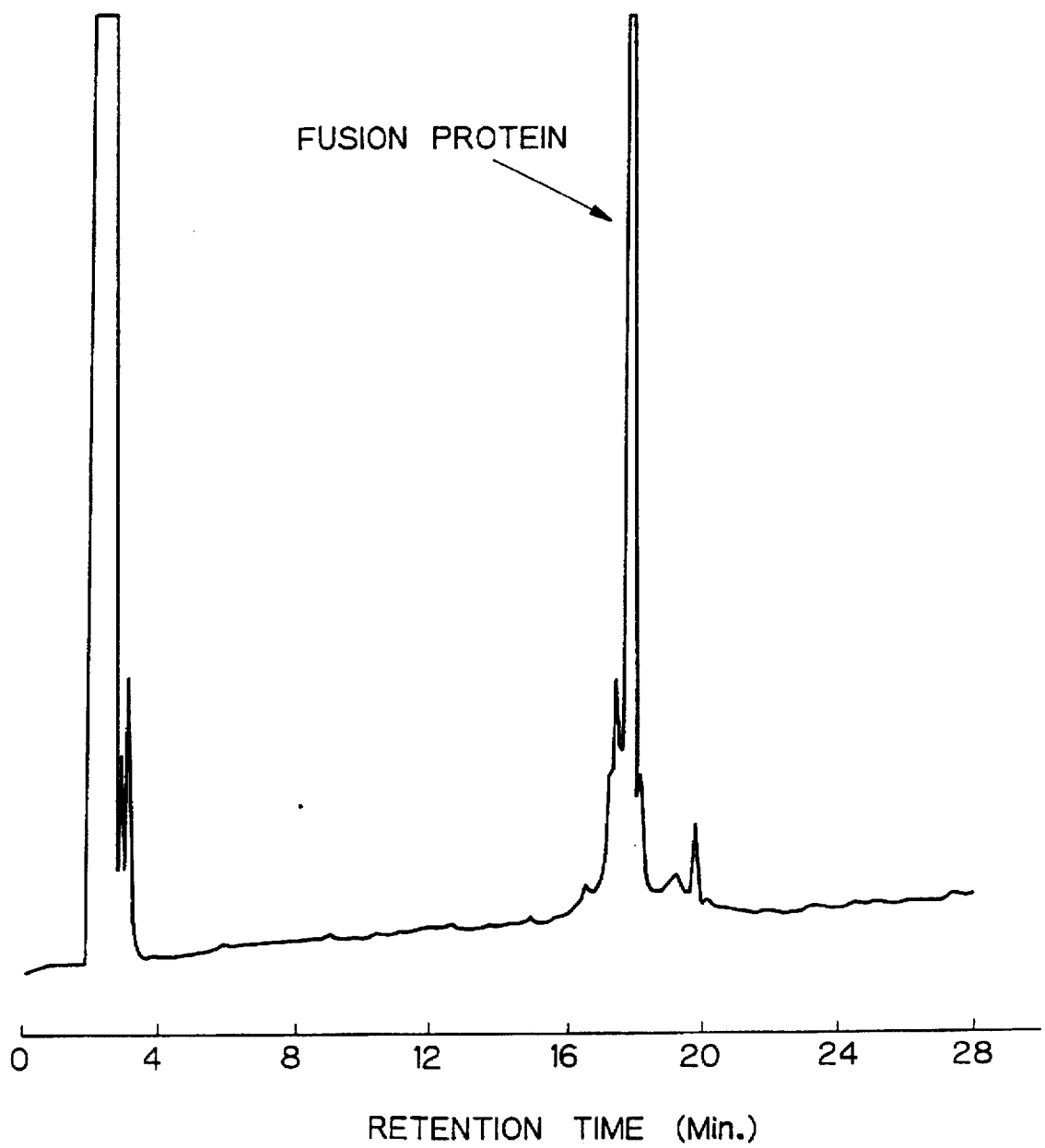
FIG. 15 indicates the elution profile of fusion protein before release of hCNP-22 in high performance liquid chromatography.
Figure 16:
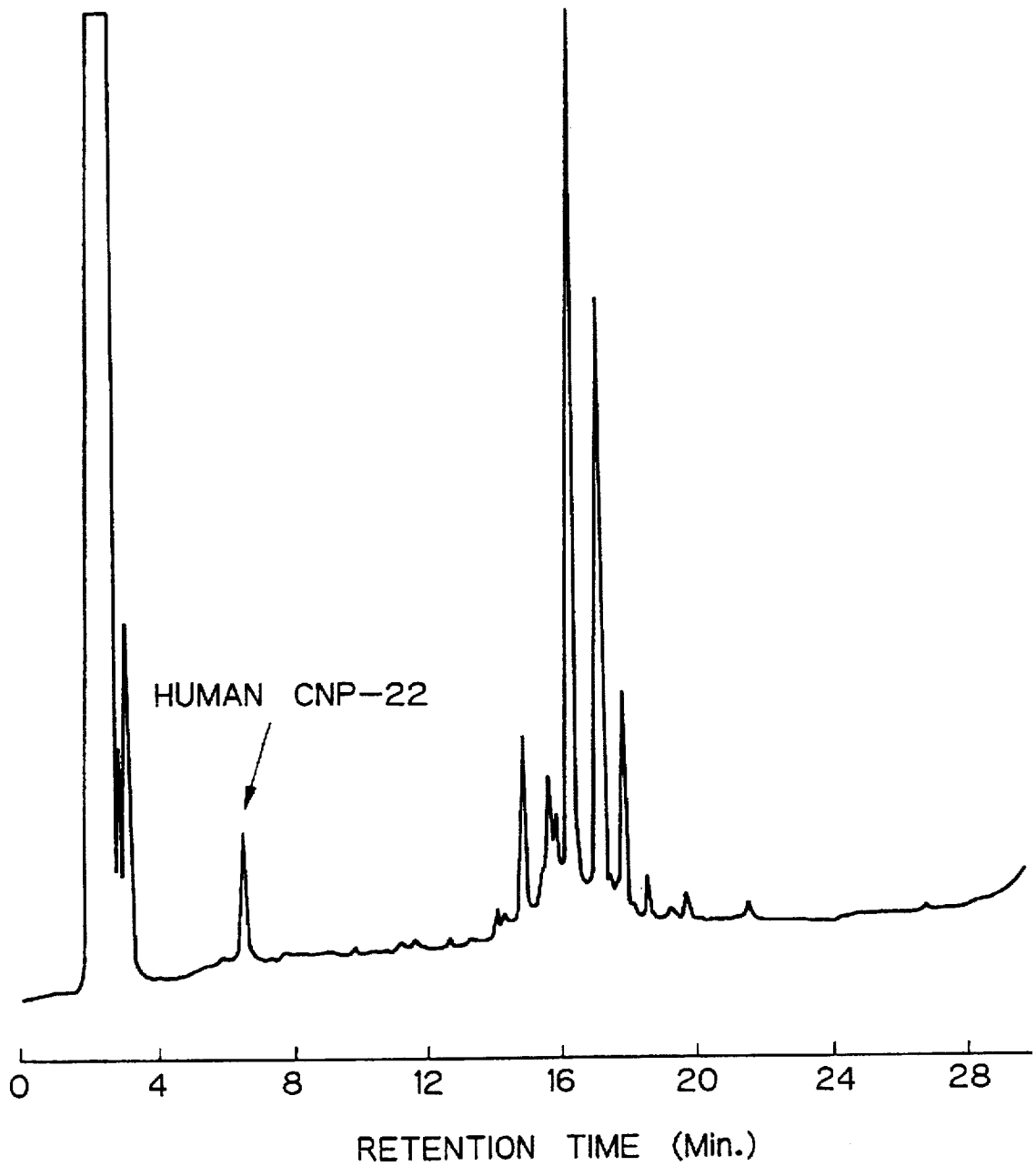
FIG. 16 indicates the elution profile of fusion protein after release of hCNP-22 in high performance liquid chromatography.

As is clear from FIGS. 15 and 16, a peak appeared from the V8 protease-digested fusion protein was coincident with that of the human CNP-22 standard, thus indicating that human CNP-22 is specifically released from the fusion protein.

Release of human CNP-22 also took place efficiently in β-gal97S4DhCNP-22R5-2 and β-gal97S4DhCNP-22R3-2, with peaks being identified that matched the human CNP-22 standard. The release efficiency of the human CNP-22 cleaved under the above-mentioned conditions was 99% for pG97S4DhCNP-22R3-2, 95% for pG97S4DhCNP-22R5-2 and 92% for pG97S4DhCNP-22RS-3.

Based on the results described above, it was verified in not only the example of human calcitonin previously reported by the inventors of the present invention, but also in this Example as well, that in the production of human CNP-22, human CNP-22 can be produced in a large amount by altering the charge of the amino acids of the linker peptide region so that the isoelectric point of the fusion protein lies within the range of 4.9–6.9, and also that CNP-22 is specifically released from fusion protein produced in a large amount in the above manner by using V8 protease.

In the present invention, it was verified for the first time by the inventors of the present invention that fusion protein can be produced in a large amounts in the form of inclusion bodies within microbial cells by designing the fusion protein so that its isoelectric point is on the acidic side, thereby allowing the production of a large amount of fusion protein containing the target peptide.

Thus, a high level of productivity of fusion protein containing the target protein can be obtained by large volume culturing using host cells obtained in the present invention, thereby allowing this to be adequately used in the production of physiologically active peptides on an industrial scale.

In addition, a method was established wherein following large volume culturing using host cells obtained in the present invention, precursor human calcitonin or human CNP-22 is released and purified from the fusion protein. Furthermore, it was demonstrated that the precursor human calcitonin was converted to the mature calcitonin in large scale, by using an amidating enzyme.

We claim:

1. A process for the production of a (target peptide) comprising:

A) culturing E. coli host cells transformed with a plasmid capable of expressing a gene coding for a fusion protein represented by the following formula:

A—L—B wherein, B is a target peptide selected from the group consisting of calcitonin precursor, atrial natriuretic peptide, brain natriuretic peptide, and C-type natriuretic peptide. A is a protective peptide comprising a fragment of 90–210 amino acids from the N-terminal of the E. coli β-galactosidase polypeptide to protect the peptide to which it is fused, and L is a linker peptide positioned between the C-terminal of said protective peptide and the N-terminal of said target peptide and is selected such that when said fusion protein is treated with an enzyme or chemical substance, said target peptide is cleaved from said linker peptide, and wherein the isoelectric point of the entire fusion protein A—L—B is adjusted to a range between 4.9 and 6.9 by including a linker peptide having basic amino acid residues;

B) obtaining an insoluble fraction comprising inclusion bodies by homogenization of said transformed E. coli host cells;

C) solubilizing said fusion protein comprised in said inclusion bodies by treatment of said insoluble fraction with a solubilizing agent; and, D) cleaving the peptide bond between the C-terminal of the linker amino acid residue and the N-terminal of the target peptide contained in said solubilized fusion protein to release said target peptide from said fusion peptide.

2. A process according to claim 1, wherein the calcitonin is human calcitonin.

3. A process according to claim 1, wherein the C-type natriuretic peptide is C-type natriuretic peptide-22.

4. The method of claim 1 wherein the fragment of the β-galactosidase polypeptide comprises the 97 amino-terminal amino acids of β-galactosidase.

5. The method of claim 4 wherein the fragment comprising the 97 amino-terminal amino acids of β-galactosidase has been mutated to change a cysteine to a serine residue and further to change four glutamic acid residues to aspartic acid residues.

* * * * *